(12) United States Patent
Lo et al.

(10) Patent No.: US 10,024,819 B2
(45) Date of Patent: Jul. 17, 2018

(54) MICROFLUIDICS WITH WIRELESSLY POWERED ELECTRONIC CIRCUITS

(75) Inventors: Yu-Hwa Lo, San Diego, CA (US); Wen Qiao, La Jolla, CA (US); Gyoujin Cho, Suncheon (KR); Hwiwon Kang, Gwangyang-Si (KR)

(73) Assignees: The Regents of the University of California, Oakland, CA (US); Industry-Academic Cooperation Foundation of Sunchon National University, Suncheon (KR)

( * ) Notice: Subject to any disclaimer, the term of this patent is extended or adjusted under 35 U.S.C. 154(b) by 1111 days.

(21) Appl. No.: 13/880,973

(22) PCT Filed: Oct. 21, 2011

(86) PCT No.: PCT/US2011/057399
§ 371 (c)(1),
(2), (4) Date: Nov. 15, 2013

(87) PCT Pub. No.: WO2012/054904
PCT Pub. Date: Apr. 26, 2012

(65) Prior Publication Data
US 2014/0061049 A1 Mar. 6, 2014

Related U.S. Application Data

(60) Provisional application No. 61/405,626, filed on Oct. 21, 2010.

(51) Int. Cl.
*G01N 27/447* (2006.01)
*B01L 3/00* (2006.01)
(Continued)

(52) U.S. Cl.
CPC .... *G01N 27/44704* (2013.01); *B01J 19/0093* (2013.01); *B01L 3/502761* (2013.01);
(Continued)

(58) Field of Classification Search
CPC .......... G01N 27/44704; G01N 27/221; G01N 27/447; B01L 2200/0652;
(Continued)

(56) References Cited

U.S. PATENT DOCUMENTS 3,790,760 A   2/1974   Stiller
3,984,307 A   10/1976  Kamentsky et al.
(Continued)

FOREIGN PATENT DOCUMENTS

EP   2078958 A1   7/2009
EP   2531832      12/2012
(Continued)

OTHER PUBLICATIONS

Chen, C., et al., "Microfluidic cell sorter with integrated piezoelectric actuator," Biomedical Microdevices, 11 (6):1223-1231, Aug. 2009.
(Continued)

*Primary Examiner* — Gurpreet Kaur
(74) *Attorney, Agent, or Firm* — Perkins Coie LLP

(57) ABSTRACT

Techniques, devices and systems are described for incorporating a printed circuit with a microfluidic device and wirelessly powering the microfluidic device. In one aspect, a microfluidic device includes a substrate with a fluidic channel to provide a path for a fluid with particles. The fluidic channel includes fluid inlet and outlet. A pair of electrodes near the inlet and the outlet guides the particles toward a center of the fluidic channel using negative-dielectrophoresis (DEP) effect in response to an alternating current (AC) frequency voltage received at the pairs of electrodes. Additional pairs of electrodes are disposed along a border of the fluidic channel between the pairs of electrodes near the inlet and the outlet of the fluidic channel to isolate a subpopulation of the particles using positive and
(Continued)

negative DEP effects in response to AC voltages of different frequencies received at different ones of the additional pairs of electrodes.

18 Claims, 18 Drawing Sheets

(51) Int. Cl.
  *B01J 19/00* (2006.01)
  *G01N 15/14* (2006.01)
(52) U.S. Cl.
  CPC .............. *B01L 3/502776* (2013.01); *B01J 2219/00853* (2013.01); *B01J 2219/00912* (2013.01); *B01L 3/502715* (2013.01); *B01L 2200/0652* (2013.01); *B01L 2200/0668* (2013.01); *B01L 2200/10* (2013.01); *B01L 2200/12* (2013.01); *B01L 2300/022* (2013.01); *B01L 2300/023* (2013.01); *B01L 2300/0645* (2013.01); *B01L 2300/0822* (2013.01); *B01L 2300/0887* (2013.01); *B01L 2400/0421* (2013.01); *B01L 2400/0424* (2013.01); *G01N 2015/1422* (2013.01)
(58) Field of Classification Search
  CPC ..... B01L 2200/0668; B01L 2400/0421; B01L 2400/0424; B01D 57/02
  See application file for complete search history.

(56) References Cited

U.S. PATENT DOCUMENTS

| | | | |
|---|---|---|---|
| 5,917,733 A | 6/1999 | Bangham | |
| 6,049,381 A | 4/2000 | Reintjes et al. | |
| 6,139,800 A | 10/2000 | Chandler | |
| 6,280,590 B1 | 8/2001 | Cheng et al. | |
| 6,294,063 B1* | 9/2001 | Becker | B01F 13/0076 204/450 |
| 6,744,038 B2 | 6/2004 | Wang et al. | |
| 6,778,724 B2 | 8/2004 | Wang et al. | |
| 6,784,420 B2 | 8/2004 | Wang et al. | |
| 6,787,018 B1 | 9/2004 | Miles et al. | |
| 6,815,664 B2 | 11/2004 | Wang et al. | |
| 6,833,542 B2 | 12/2004 | Wang et al. | |
| 6,909,824 B1 | 6/2005 | Messica et al. | |
| 6,936,811 B2 | 8/2005 | Kibar | |
| 7,068,874 B2 | 6/2006 | Wang et al. | |
| 7,157,271 B2 | 1/2007 | Ryu et al. | |
| 7,160,687 B1 | 1/2007 | Kapur et al. | |
| 7,245,379 B2 | 7/2007 | Schwabe | |
| 7,298,478 B2 | 11/2007 | Gilbert et al. | |
| 7,355,699 B2 | 4/2008 | Gilbert et al. | |
| 7,492,522 B2 | 2/2009 | Gilbert et al. | |
| 7,576,861 B2 | 8/2009 | Gilbert et al. | |
| 7,658,829 B2 | 2/2010 | Kanagasabapathi et al. | |
| 7,701,580 B2 | 4/2010 | Bassler et al. | |
| 7,745,221 B2 | 6/2010 | Butler et al. | |
| 7,746,466 B2 | 6/2010 | Godin et al. | |
| 7,767,444 B2 | 8/2010 | Liu et al. | |
| 7,870,964 B2 | 1/2011 | Gilbert et al. | |
| 8,026,054 B2 | 9/2011 | Sharma et al. | |
| 8,270,781 B2 | 9/2012 | Lo et al. | |
| 8,277,764 B2 | 10/2012 | Gilbert et al. | |
| 8,373,860 B2 | 2/2013 | Kiesel et al. | |
| 8,426,209 B2 | 4/2013 | Butler et al. | |
| 8,629,981 B2 | 1/2014 | Martini et al. | |
| 8,691,164 B2 | 4/2014 | Butler et al. | |
| 8,717,569 B2 | 5/2014 | Lo et al. | |
| 8,822,207 B2 | 9/2014 | Foster et al. | |
| 8,993,311 B2 | 3/2015 | Foster et al. | |
| 9,011,797 B2 | 4/2015 | Gilbert et al. | |
| 9,134,221 B2 | 9/2015 | Lo et al. | |
| 2002/0011097 A1 | 1/2002 | Kuderer et al. | |
| 2002/0108859 A1 | 8/2002 | Wang et al. | |
| 2002/0113204 A1 | 8/2002 | Wang et al. | |
| 2002/0115163 A1 | 8/2002 | Wang et al. | |
| 2002/0121443 A1 | 9/2002 | O'Connell | |
| 2002/0122167 A1 | 9/2002 | Riley et al. | |
| 2002/0123112 A1 | 9/2002 | Wang et al. | |
| 2002/0137059 A1 | 9/2002 | Wu et al. | |
| 2002/0160470 A1 | 10/2002 | Zhang | |
| 2003/0124516 A1 | 7/2003 | Chung et al. | |
| 2003/0137666 A1 | 7/2003 | Johnson | |
| 2003/0159999 A1 | 8/2003 | Oakey et al. | |
| 2003/0194755 A1 | 10/2003 | Schnabel et al. | |
| 2003/0211461 A1 | 11/2003 | Kariv et al. | |
| 2003/0215791 A1 | 11/2003 | Garini et al. | |
| 2004/0009540 A1 | 1/2004 | Soohoo et al. | |
| 2004/0023310 A1 | 2/2004 | Kariv et al. | |
| 2004/0033539 A1 | 2/2004 | Schnabel et al. | |
| 2004/0053209 A1 | 3/2004 | Kariv et al. | |
| 2004/0072278 A1 | 4/2004 | Chou et al. | |
| 2004/0161772 A1 | 8/2004 | Bohm et al. | |
| 2005/0023137 A1 | 2/2005 | Bhullar et al. | |
| 2005/0036139 A1 | 2/2005 | Johnson | |
| 2005/0066246 A1* | 3/2005 | Maltseff | G01R 31/303 714/733 |
| 2005/0068536 A1 | 3/2005 | Schwabe | |
| 2005/0105077 A1 | 5/2005 | Padmanabhan et al. | |
| 2005/0112541 A1 | 5/2005 | Durack et al. | |
| 2005/0164372 A1 | 7/2005 | Kibar | |
| 2006/0060767 A1 | 3/2006 | Wang et al. | |
| 2006/0066837 A1 | 3/2006 | Ortyn et al. | |
| 2006/0117563 A1 | 6/2006 | Sugahara | |
| 2006/0192955 A1 | 8/2006 | Jorgenson et al. | |
| 2006/0197033 A1 | 9/2006 | Hairston et al. | |
| 2006/0282752 A1 | 12/2006 | Kuroda | |
| 2007/0086918 A1 | 4/2007 | Hartley et al. | |
| 2007/0117086 A1 | 5/2007 | Evans et al. | |
| 2007/0128686 A1 | 6/2007 | Jing et al. | |
| 2007/0140638 A1 | 6/2007 | Yang et al. | |
| 2007/0159627 A1 | 7/2007 | Johnson | |
| 2007/0182565 A1 | 8/2007 | Lee et al. | |
| 2007/0240495 A1* | 10/2007 | Hirahara | B01L 3/502746 73/53.01 |
| 2008/0233635 A1 | 9/2008 | Evans et al. | |
| 2008/0302732 A1 | 12/2008 | Soh et al. | |
| 2008/0319680 A1 | 12/2008 | Fox et al. | |
| 2009/0027666 A1 | 1/2009 | Godin et al. | |
| 2009/0042737 A1 | 2/2009 | Katz et al. | |
| 2009/0155832 A1 | 6/2009 | Lo et al. | |
| 2009/0190121 A1 | 7/2009 | Hegyi et al. | |
| 2009/0194705 A1 | 8/2009 | Kiesel et al. | |
| 2009/0195773 A1 | 8/2009 | Bassler et al. | |
| 2009/0207576 A1* | 8/2009 | Gardner | H01F 10/16 361/782 |
| 2010/0018310 A1 | 1/2010 | Mutharasan et al. | |
| 2010/0051828 A1 | 3/2010 | Doemer et al. | |
| 2010/0072285 A1* | 3/2010 | Nishijima | G06K 19/0707 235/492 |
| 2010/0101983 A1* | 4/2010 | Butler | B82Y 30/00 209/552 |
| 2010/0108577 A1 | 5/2010 | Wang et al. | |
| 2010/0117007 A1 | 5/2010 | Kibar | |
| 2010/0155572 A1 | 6/2010 | Kiesel et al. | |
| 2011/0039258 A1 | 2/2011 | McNeeley et al. | |
| 2011/0086769 A1 | 4/2011 | Oliphant et al. | |
| 2011/0196637 A1 | 8/2011 | Sharpe et al. | |
| 2012/0009619 A1 | 1/2012 | Gilbert et al. | |
| 2012/0011097 A1 | 1/2012 | Matsumura et al. | |
| 2012/0012508 A1 | 1/2012 | Deshpande et al. | |
| 2012/0045763 A1 | 2/2012 | Sharma et al. | |
| 2012/0077191 A1 | 3/2012 | Gunning et al. | |
| 2012/0078531 A1 | 3/2012 | Lo et al. | |
| 2012/0138513 A1 | 6/2012 | Johnson et al. | |
| 2012/0190105 A1 | 7/2012 | Foster et al. | |
| 2012/0202237 A1 | 8/2012 | Sedoglavich et al. | |
| 2012/0255373 A1 | 10/2012 | Foster et al. | |
| 2012/0261013 A1 | 10/2012 | Gilbert et al. | |
| 2012/0277902 A1 | 11/2012 | Sharpe et al. | |
| 2012/0307244 A1 | 12/2012 | Sharpe et al. | |
| 2013/0004987 A1 | 1/2013 | Lo et al. | |

(56) References Cited

U.S. PATENT DOCUMENTS

| | | | |
|---|---|---|---|
| 2013/0016335 A1 | 1/2013 | Lo et al. | |
| 2013/0083315 A1 | 4/2013 | Lo et al. | |
| 2013/0118904 A1* | 5/2013 | Dickerson | G01N 27/447 204/547 |
| 2013/0171683 A1 | 7/2013 | Durack et al. | |
| 2013/0313170 A1 | 11/2013 | Bohm et al. | |
| 2013/0334407 A1 | 12/2013 | Perrault, Jr. et al. | |
| 2014/0048417 A1* | 2/2014 | Heller | G01N 27/447 204/547 |
| 2014/0244217 A1 | 8/2014 | Lo et al. | |
| 2014/0251879 A1 | 9/2014 | Deshpande et al. | |
| 2015/0211979 A1 | 7/2015 | Lo et al. | |
| 2016/0003729 A1 | 1/2016 | Lo et al. | |

FOREIGN PATENT DOCUMENTS

| | | |
|---|---|---|
| EP | 2671065 | 12/2013 |
| EP | 2872887 A1 | 5/2015 |
| KR | 1020070049974 | 5/2007 |
| KR | 1020090056574 | 6/2009 |
| WO | WO-9405775 A1 | 3/1994 |
| WO | WO-2002059577 | 8/2002 |
| WO | WO-2007/051170 A2 | 5/2007 |
| WO | WO-2010/104993 A2 | 9/2010 |
| WO | WO-2012083250 A2 | 6/2012 |
| WO | WO-2012106645 A1 | 8/2012 |
| WO | WO-2012154614 A1 | 11/2012 |
| WO | WO-2013010134 A2 | 1/2013 |
| WO | WO-2013192342 A1 | 12/2013 |

OTHER PUBLICATIONS

Cho, S., et al., "Micro-fabricated Fluorescence-Activated Cell Sorter," Annual International Conference of the IEEE Engineering in Medicine and Biology Society, pp. 1075-1078, Sep. 3-6, 2009.
Cho, S., et al., "Microfluidic Photonic Integrated Circuits," Optoelectronic Materials and Devices, vol. 7135, pp. 1-17, Jan. 2008.
Cho, S., et al., "Optofluidic Waveguides in Teflon AF-Coated PDMS Microfluidic Channels," IEEE Photonics Technology Letters, 21(15)1057-1059, Aug. 1, 2009.
Fu, A. Y., et al., A Microfabricated Fluorescence-Activated Cell Sorter, Nature Biotechnology, vol. 17, pp. 1109-1111, Nov. 1999.
Godin, J., et al., "Microfluidics and photonics for Bio-System-on-a-Chip: A review of advancements in technology towards a microfluidic flow cytometry chip," Journal of Biophotonics, 1(5):355-376, Oct. 2008.
Lee, G.-B., et al., "Micro Flow Cytometers with Buried SU-8/SOG Optical Waveguides," Sensors and Actuators A: Physical, 103(1):165-170, Jan. 2003.
Lien et al. IEEE "A Prealigned Process of Integrating Optical Waveguides With Microfluidic Devices," IEEE Photonics Technology Letters, 16(6):1525-1527, Jun. 2004.
Lien et al., "High-Sensitivity Cytometric Detection Using Fludic-Photonic Integrated Circuits with Array Waveguides," IEEE Journal of Selected Topies in Quantum Electronics, vol. 11, No. 4, Jul./Aug. 2005.
Lien, V., et al., "Fluidic Photonic Integrated Circuit for In-Line Detection," Applied Physics Letters, 87(19):194106(1-3), Nov. 2005.
Lien, V., et al., "Microfluidic-photonic-dielectrophoretic integrated circuits for biophotonic sensing," The 17th Annual Meeting of the IEEE Lasers and Electro-Optics Society, vol. 2, pp. 533-534, Nov. 2004.
Lo et al. (IEEE Journal of Selected Topics in Quantum Electronics, vol. 11 No. 4).
Qiao et al., Wirelessly powered microfluidic dielectrophoresis devices using printable RF circuits, The Royal Society of Chemistry, Lab Chip, 2011, 11, 1075-1080.
Tung, Y.-C., et al., "PDMS-based opto-fluidic micro flow cytometer with two-color, multi-angle fluorescence detection capability using PIN photodiodes," Sensors and Actuators B, 98(2-3):356-367, Mar. 2004.
Zhang, et al., "Time-of-Flight Optophoresis Analysis of Live Whole Cells in Microfludic Channels," Biomedical Microdevices 6:1, 11-21, 2004.
International Search Report and Written Opinion dated Nov. 1, 2007 for International Application No. PCT/US2006/060313, filed Oct. 27, 2006 (4 pages).
International Search Report and Written Opinion dated Oct. 26, 2010 for International Application No. PCT/US2010/026884, filed Mar. 10, 2010 (10 pages).
International Search Report and Written Opinion of International Application No. PCT/US2011/057399; dated Jun. 28, 2012; 18 pages.
Office Action for Korean Patent Application No. 10-2013-7013040, dated Aug. 27, 2017, 5 pages.

\* cited by examiner

MICROFLUIDICS WITH WIRELESSLY POWERED ELECTRONIC CIRCUITS

PRIORITY CLAIM AND RELATED PATENT APPLICATION

This patent document claims the benefit of U.S. Provisional Application No. 61/405,626, filed Oct. 21, 2010, which is incorporated by reference as part of the disclosure of this document.

TECHNICAL FIELD

This patent document relates to microfluidic technologies and microfluidic devices, methods and systems that include printed circuits.

BACKGROUND

Microfluidic technologies have been used to implement the lab-on-a-chip concept by reducing a bench top chemical or biomedical experimental setup to a single die. The concept of lab-on-a-chip can potentially increase test throughput with a much smaller amount of reagents, and at the same time, produce a smaller amount of wastes and bio hazardous materials than conventional methods. As a result, the lab-on-a-chip concept has various applications in chemical engineering, food industry, drug discovery, point-of-care diagnostics, genomics, and biomedical research in general.

SUMMARY

Techniques, devices and systems are described for incorporating printed electronic circuits into fluidic or microfluidic devices to bridge the process incompatibility between electronics and fluid devices.

On aspect of the disclosed embodiments relates to a microfluidic device that includes a substrate comprising a fluidic channel to provide a path for a fluid with suspended particles, where the fluidic channel includes an inlet and an outlet for the fluid. The microfluidic device also includes a pair of electrodes positioned near the inlet and the outlet of the fluidic channel to guide the particles toward a center of the fluidic channel using negative dielectrophoresis (DEP) effect in response to an alternating current (AC) frequency voltage received at the pair of electrodes. Furthermore, the microfluidic device includes additional electrodes positioned along a border of the fluidic channel between the two pairs of electrodes to isolate a subpopulation of the particles using positive and negative DEP effects in response to AC voltages of different frequencies received at different ones of the additional electrodes.

In some embodiments, the fluidic channel comprises a permanent fluidic channel formed on the substrate. In another embodiment, the fluidic channel comprises a removable fluidic channel disposed over the substrate, wherein the substrate is patterned to provide a path for a fluid.

In further embodiments, the microfluidic device also includes an integrated circuit configured to supply the AC voltages of different frequencies to the different ones of the additional electrodes and AC voltages to the pair of electrodes at the inlet and the outlet of the fluidic channel. In these embodiments, an inductor is configured to couple power from an external transmitter to the integrated circuit. In one example embodiment, the inductor comprises an antenna. For instance, the antenna can include loops to inductively couple the power from the external transmitter to the integrated circuit. Moreover, the antenna can be configured to couple the power back to the external transmitter from the integrated circuit.

According to some embodiments, the integrated circuit includes one or more of a memory, a register, a processor and a switch. In certain embodiments, the integrated circuit is configured: to turn on and off the AC voltages applied to the pair of electrodes and each of the additional electrodes, to store data comprising at least one of impedance, phase, or current, and/or to transmit data to an external device.

Another aspect of the disclosed embodiments relates to a method of isolating a subpopulation of particles suspended in a fluid that includes flowing a fluid with suspended particles through an inlet of a fluidic channel in a microfluidic device, where the fluidic channel has a pair of electrodes positioned near the inlet and at an outlet of the fluidic channel. This method further includes applying an AC voltage to the pair of electrodes to guide the particles toward a center of the fluidic channel using negative DEP effect, and also applying AC voltages of different frequencies at different ones of additional electrodes positioned along a border of the fluidic channel between the pairs of electrodes to isolate a subpopulation of the particles using positive and negative DEP effects. In one example embodiment, this method further includes providing power to the microfluidic device over a wireless medium.

Another aspect of the disclosed embodiments relates to a microfluidic device that includes a substrate having a fluidic channel with an inlet to receive a fluid with particles suspended in the fluid and one or more sheath flow inlets to receive sheath flow. Such a microfluidic device also includes at least one pair of electrodes positioned near the inlet, where the at least one pair of electrodes is/are configured to electrophoretically separate suspended particles when supplied with a DC voltage. This a microfluidic device further includes a series of electrodes arranged along the fluidic channel, where the series of electrodes are configured to sort the separated particles using positive and negative DEP effect when supplied with AC voltages at different frequencies.

In some embodiments, the fluidic channel has a free-flow design to allow the fluid sample to spread out transverse to a flow direction. In another example embodiment, the at least one pair of electrodes are configured to separate the particles into groups according to one or more of charge, shape, and mass based on an EP effect. In yet another example, embodiment, each pair of the series of electrodes is configured to receive an AC voltage that is different in frequency from at least another pair of the series of electrodes.

According to another example embodiment, each pair of the series of electrodes has an asymmetric geometry. Moreover, in some embodiments, the series of electrodes are configured to attract particles experiencing positive DEP effect to an edge of the series of electrodes, and divert particles experiencing negative DEP effect toward paths between the series of electrodes where a gradient of an electric field is zero. In still another embodiment, the microfluidic device further comprises an integrated circuit configured to produce the AC voltages of different frequencies to the different ones of the additional electrodes and the AC voltages to the at least one pair of electrodes at the inlet and the outlet of the fluidic channel, as well as an inductor configured to couple power from an external transmitter to the integrated circuit.

Another aspect of the disclosed embodiments relates to a method of sorting particles in a microfluidic device that includes introducing a fluidic sample comprising suspended particles through a sample inlet of a fluidic channel in the microfluidic device and introducing a sheath flow through one or more sheath flow inlets. This method further includes separating the particles electrophoretically by DC biasing two pairs of electrodes near the sample inlet, and sorting the separated particles using negative and positive DEP effects using a series of electrodes arranged along the fluidic channel, where at least one pair of electrodes within the series of electrodes receives an ac voltage at a frequency that is different from ac voltage frequency received by another electrode in the series of electrodes. In one example embodiment, this method further includes providing power to the microfluidic device over a wireless medium.

Another aspect of the disclosed embodiments relates to a microfluidic device that includes a substrate having a fluidic channel with a sample inlet to receive a sample solution with suspended particles and a sheath flow inlet, the sample inlet and the sheath flow inlet arranged with respect to each other to allow sheath flow into the fluidic channel and to confine at least a portion of the suspended particles in a lower part of the fluidic channel before a sorting junction. This microfluidic device also includes a pair of electrodes positioned near the sample inlet and configured to generate a non-uniform field to direct particles experiencing a negative DEP effect into an upper chamber and direct particles subject to a positive DEP effect into a lower chamber. The microfluidic device additionally includes one or more parallel array of electrodes configured to further subdivide the particles within each chamber using a traveling DEP force generated in response to voltages of different phases applied to different electrodes of a given parallel array of electrodes. In one example embodiment, the device also includes an integrated circuit configured to supply voltages of different phases to the different electrodes of the given array of electrodes and the voltage to the pairs of electrodes near the inlet of the fluidic channel, as well as an inductor configured to couple power from an external transmitter to the integrated circuit.

Another aspect of the disclosed embodiments relates to method of sorting particles that includes receiving a sample fluid with suspended particles at a sample inlet of a fluidic channel and receiving a sheath flow from a sheath flow inlet arranged with respect to the sample inlet to confine at least a portion of the suspended particles in a lower part of the fluidic channel before a sorting junction. This method further includes generating a non-uniform field at a pair of electrodes near the sample inlet to direct particles experiencing a negative DEP effect into an upper chamber and direct cells subject to a positive DEP effect into a lower chamber, and subdividing the particles using a traveling DEP force generated by one or more parallel array of electrodes by applying voltages of different phases to different electrodes of a given parallel array of electrodes.

Another aspect of the disclosed embodiments relates to microfluidic device that includes a substrate patterned to form one or more channels to carry fluids, and microfluidic components formed on the substrate and structured to control a fluidic flow in the one or more channels. This microfluidic device also includes a circuit formed on the substrate and electrically coupled to one or more of the microfluidic components to supply electrical power to the one or more of the microfluidic components. The circuit includes an antenna to wirelessly receive an electromagnetic wave signal and to use the wirelessly received electromagnetic wave signal to generate the supplied electrical power to the one or more of the microfluidic components.

DETAILED DESCRIPTION

Figure 1A:
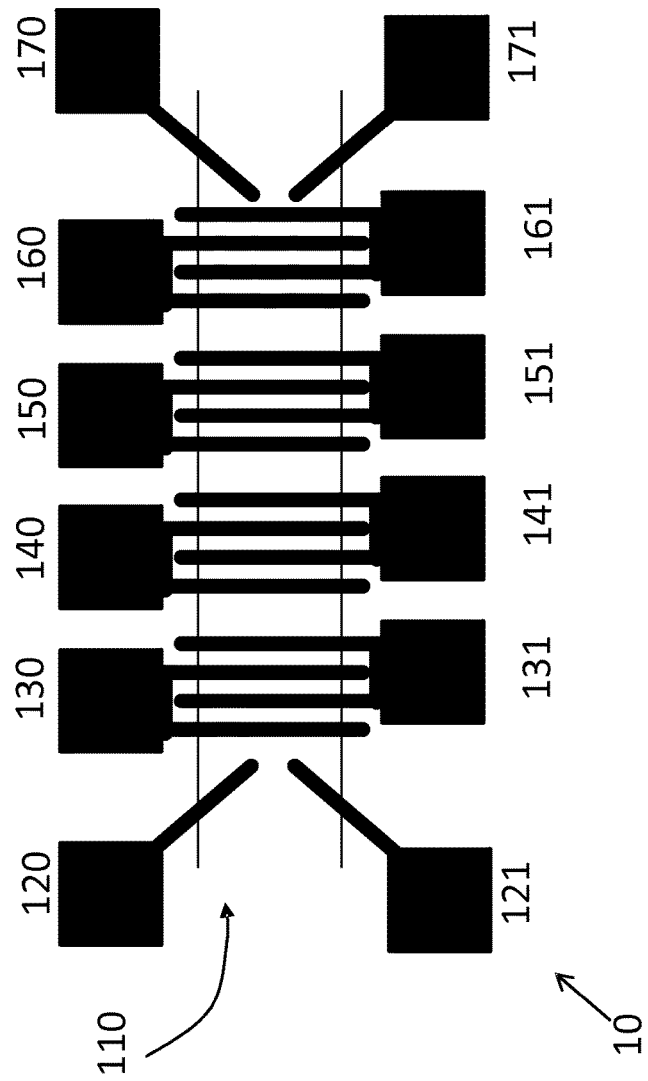
FIG. 1(a) illustrates a microfluidic device in accordance with an example embodiment.

Incorporating microfluidics in lab-on-a-chip provides the ability to transport, store, and manipulate fluid with suspended bioparticles and chemicals in a much smaller volume, in the range of microliters, nanoliters, picoliters, or even femtoliters, compared to conventional methods using pipettes and test tubes. Microfluidics presents a useful and versatile technology platform to use interactions of objects in the fluid with other physical mechanisms such as optical, acoustic, magnetic, and electrical fields for various sample sensing, diagnostic, processing, manipulation and other operations and functionalities. Fluorescence, scatterings, surface plasmonics, and surface enhanced Raman scattering are examples of optical bio- and chemical-detection in microfluidic environment. These methods can reveal important information about the properties of the species under test. Acoustic and electromagnetic fields can interact with the species of proper densities and magnetic properties remotely, producing useful functions such as sample sorting and separation. Moreover, the interaction between the suspended objects and the applied electric field can be identified and described. Besides using electrical current to heat the sample in miniaturized polymerase chain reaction (PCR) systems, a suspended object can interact with the electric field in various manners, including, for example, electrophoresis effect (EP), direct current-dielectrophoresis effect (DC-DEP), and Alternating current-dielectrophoresis (AC-DEP) effect.

Using a suspended homogeneous spherical particle as an example, the velocity of the particle relative to the fluid under an external electric field E can be represented as $$v_{EP} = \frac{qE}{6\pi\mu a}, \tag{1}$$

where $v_{EP}$, is the velocity of the particle relative to the fluid, q is the total amount of charge of the particle, μ is the viscosity of the fluid, and a is the radius of the particle. However, for electrokinetic motion of a charged particle inside a microchannel, the electroosmotic flow (EOF) effect should be considered together with the electrophoresis (EP) effect as these two effects are not independent of each other (i.e. the fluid medium may not be static under the electric field). As a result, the apparent velocity of the electrokinetic motion of a spherical particle is given, according to the Helmholtz-Smoluchowski equation, by $$v_P = \frac{\varepsilon_m(\xi_w - \xi_p)E}{\mu}, \tag{2}$$

where $v_p$ is the apparent velocity of the charged particle in a microfluidic channel under an electric field, E. $\varepsilon_m$ is the permittivity of the suspending medium, and $\xi_w$ and $\xi_p$ are zeta potentials of the microfluidic channel wall and the particle, respectively. Therefore, the particle velocity is proportional to the magnitude of E-field, inversely proportional to the viscosity of the medium, and the difference in zeta potential between the channel wall material and the suspended particle. The relationship in Eq. (2) applies to homogeneous spherical particles and does not take into account of other shapes of the particles. The apparent velocity due to the EP effect depends on the shape of the particle. It has been demonstrated that using designs of microcapillary electrophoresis, microfluidic free-flow electrophoresis (FFE), free-flow zone electrophoresis (FFZE), free-flow isoelectric focusing (FFIEF), free-flow isotachophoresis (FFITP), and free-flow field step electrophoresis (FFFSE), micro- and nano-arrays, people have demonstrated separation and sorting of mammalian cells, microbes, virus, immunoassay, proteins, DNAs, etc.

In addition to the electrophoresis effect, the suspended particle may experience the dielectrophoresis (DEP) effect. The DEP force of a homogeneous spherical particle can be represented as $$F_{DEP} = 2\pi\varepsilon_m a^3 K_{CM}(\varepsilon,\sigma,\omega)\nabla|E|^2 \tag{3},$$

where $K_{CM}$ is the Clausius-Mossotti factor and is a function of permittivity, $\varepsilon$, conductivity σ, and frequency, ψ, of the E-field. As such, the value of $K_{CM}$ depends on properties of the particle and the medium, and can be represented as:

$$K_{CM} = \frac{\varepsilon_p^* - \varepsilon_m^*}{\varepsilon_p^* + 2\varepsilon_m^*}, \tag{4}$$

where $\varepsilon^*_{p,m}$ are the complex permittivities of the particle, p, and medium, m, and are given by $$\varepsilon_{p,m}^* = \varepsilon_{p,m} + \frac{\sigma_{p,m}}{j\omega}, \tag{5}$$

where $\varepsilon$ is the real part of the permittivity and σ is the conductivity. As noted earlier, α is the radius of the particle. As shown in Eq. (3), the DEP effect is proportional to the gradient of the magnitude of the electric field. In microfluidics, electrodes can be positioned close together to create a large enough gradient to make the DEP effect more pronounced than it is in the bulk medium. In the most general condition where both EP and DEP effects are taken into account, the net apparent velocity of a suspended particle can be written as $$v_P = \frac{\varepsilon_m(\xi_w - \xi_p)E}{\mu} + \frac{\varepsilon_m a^2 K_{CM}}{3\mu}\nabla|E|^2. \tag{6}$$

Due to the square dependence of the radius of the particle, the DEP effect can be often used to separate larger bioparticles such as cells, fungi, parasite, and bacteria. Since water or typical electrolyte has a very large DC dielectric constant (approximately 78), the Clausius-Mossotti factor KCM is often negative hence the particle tends to move away from the places where the field gradient is strongest, so called negative DEP (n-DEP) effect. Again, because of the strong size dependence, the DC-DEP effect can be highly effective in separating particles by their size. However, high applied DC voltage may cause hydrolysis of water and mixture of particles of similar size due to Brownian motions. It can be desirable for certain applications to use AC-DEP effect with an applied AC voltage. At sufficiently high frequencies, the electrolyte hydrolysis does not occur or its effect is insignificant so that a sufficient magnitude of the E-field can be applied between electrodes. The resolution and flexibility of sample sorting and separation can be greatly enhanced by taking advantage of the dispersion properties of the medium and the sample. The complex permittivities of medium and particle both vary with frequency. At a certain frequency range, one or more particles may experience positive AC-DEP force and one or more other particles may experience negative AC-DEP. As a result, the particles experiencing the positive AC-DEP may be attracted to the edge of the electrode(s) where the field gradient is designed to be the strongest, and the other particles experiencing negative AC-DEP are expelled from the electrodes. After washing away the unwanted particles, the frequency of the applied voltage can be modified into the negative AC-DEP regime so that the originally attracted particles are now released and collected. If the microfluidic devices are designed to have multiple stages of electrodes each operating at different frequencies, different kinds of biological particles may be separated into different locations and be released and collected in sequence, thus producing pure bio-specimens.

The applications of DEP effects in microfluidics are numerous and unique. For instance, in pathology and for food water inspection, the AC-DEP effects can separate pathogens from the samples to detect low concentration of bacteria. For cancer diagnosis and monitoring of the effectiveness of chemotherapy for cancer, the AC-DEP effect can be used to collect extremely rare circulating cancer cells (CTCs) from peripheral blood. For genetics, AC DEP can help isolate single cells for single-cell analysis such as single-cell genotyping, which may reveal important information about cancer stem cells. For epigenetics, AC-DEP may be used to separate chromatins from the DNA samples and sort chromatins according to the life cycle of the cells. For food industry, AC-DEP may be used to separate viable yeast cells from non-viable yeast cells. In general, many diseases that can be detected in blood, sputum, mucus, urine, and body fluids may be detected at a much higher sensitivity in microfluidics utilizing the electrophoresis and dielectrophoresis effects.

The disclosed methods, devices and systems incorporate printed electronic circuits into fluidic or microfluidic devices to bridge the process incompatibility between electronics and fluid devices. The described techniques, devices and systems go beyond mere passive electrodes. Rather, active electronic components such as transistors and diodes and integrated circuits (ICs) can be incorporated with the lab-on-a-chip microfluidic circuits. As a result, a clinics technician can take advantage of the EP or DEP effect without having to make all the electric connections to the "lab-on-a-chip slide" or figure out the operation of multiple electronic instruments to set the voltage, current, frequency, phase, and other parameters. By incorporating active electronics with the lab-on-a-chip fluidic or microfluidic circuits, a practical, economical and error proof system can be implemented.

The described technical solution to the technical problem of adopting lab-on-a-chip microfluidic devices in point-of-care clinics can include the following aspects: (a) incorporation of printed integrated circuits into the microfluidic devices and (b) powering the lab-on-a-chip device wirelessly. Unlike traditional silicon based ICs, the printed integrated circuit offers significant cost reduction with the promise of approaching 1 cent per circuit and can be fabricated on various substrates (glass, polymer, plastic, etc.) used in microfluidics. Powering the circuit wirelessly can completely eliminate the need for making electrical connections and wiring by users, thus greatly simplifying the operation and reducing the chance for errors.

By incorporating the printed electronic circuits into fluidic or microfluidic devices, systems and methods can be implemented for trapping, separating, sorting, and detecting bioparticles including bacteria, microbes, virus, DNAs, proteins, parasites, pathogens, yeast, fungi, mammalian cells, beads and nano particles in order to monitor health, diagnose diseases, and test water and food quality. As described in detail below, the described methods, devices and systems can encompass a variety of different embodiments of microfluidic-electronic lab-on-a-chip circuits and similar devices, as well as systems that implement those circuits and devices. Such circuits and devices can be powered wirelessly and employed for a variety of purposes such as, for example, detecting the presence of biological particles and flow cytometry. Additionally, the described methods, devices and systems can encompass various techniques of operating and manufacturing such integrated circuits and devices (and/or systems that implement those integrated circuits and devices). In at least some embodiments, microfluidic-electrophoretic/dielectrophoretic integrated circuits can be fabricated by way of a process involving roll-to-roll printing, inkjet printing, micro-molding, polymer bonding, and capillary filling, or combinations thereof.

Printed integrated circuits can be incorporated into all types of microfluidic devices which might be sophisticated lab-on-a-chip devices or simple glass slide with a cover slip, forming a free-flow microfluidic device when the space between the cover slip and the glass slide is sufficiently small. The integrated circuit (IC) can include dozens or hundreds of active and passive electronic components including resistors, capacitors, inductors, diodes, transistors, processors, busses, etc. The printed IC may also have multiple contact electrodes in different geometries and configurations in favor of electrokinetics of bioparticles. At each pair of electrodes, output voltages of different magnitude, polarity, frequency, and waveform may be established. For instance, an array of electrodes with AC outputs at different frequencies may trap specific cell types at delegated locations via positive AC DEP effects. A pair of electrodes that produces a low frequency or DC voltage may "focus" the bioparticles to the center stream of the flow based on the negative DEP effect, and such flow focusing is essential to lab-on-a-chip flow cytometers. An electric pulse may also cause on-chip cell lysis to extract organelles and genetic materials such as chromosomes and proteins from targeted cell types.

Without an integrated circuit, one can at best control the geometry of the electrodes and all the desired signals have to be provided externally from an array of electronic instrument such as power supply, waveform generator, frequency synthesizer, amplifier, and filter. This makes the operation costly, complex, and prone to errors, unsuitable for clinical applications. When all these functions are incorporated into an electronic circuit, the device can become self contained and compact, requiring no external equipment and knowledge in electronics to operate. Since the printed ICs may also include memories and signal processing capabilities, more intelligence can be built onto the microfluidic-electronic device to create "smart slides" or smart "lab-on-a-chip" devices.

On the printed circuit, a printed inductor, such as an antenna can be included to wirelessly power the integrated circuits incorporated with the microfluidic devices. The number of turns, the area enclosed by the inductor, and the resistance of the metal wires determine the power coupling efficiency and the Ohmic loss. The AC power coupled into the inductor produces an AC voltage signal at the same frequency as the input signal from the transmitter. The AC voltage is then converted to a DC output by a rectifier circuit made of diodes and capacitors. The DC output signal can then be used as the main power supply to drive the integrated circuit. The wireless transmitter contains an oscillator at the specific frequency (e.g. 13.56 MHz). Via a transmitting antenna, the transmitter irradiates the receiver circuit with RF energy. The amount of RF energy transmitted to the receiver depends on the antenna (inductor) design, the power of the transmitter, and the distance between the transmitter and the receiver. In one aspect, some components of commercial RFID systems can be used to enable one or more operation of the microfluidic-electronic device. For example, an RFID reader can be used to provide power to the microfluidic-electronic device. This approach fully leverages the extensive investment in RFID industry. In most situations, an RFID reader can transmit only a very limited amount of power (in the order of milliwatts to microwatts) to the circuit next to the reader, thus limiting the amount of functions the circuit can do. However, the power limit does not impose a significant constraint on operations of the disclosed microfluidic-electronic device, mainly because the amount of power required to control bioparticles is significantly lower than that in other situations. Fundamentally, the DC or AC current in microfluidics is carried by ions, molecules, and cells. Since the mobility of these charge carriers is several orders of magnitude lower than that of electrons in semiconductor, the peak current level may be in the order of nanoampers. As a result, the power consumption for cell sorting, separation, or lysing could be no more than microwatts. Due to the low power consumption, fluidic medium will suffer from minimum temperature rise, critical to biodetection involving proteins and cells.

FIG. 1(a) illustrates a microfluidic device 10 in accordance with an example embodiment. The microfluidic device of FIG. 1(a) is capable of allowing trapping of bioparticles responsive to electric signals of different frequencies. A fluidic channel 110 is formed on a glass or polymer substrate (not shown). The fluidic channel 110 may be a permanently formed channel through bonding or molding process or a temporary structure formed by placing a cover slip over a patterned substrate to provide a path for the fluid with suspended particle. An AC voltage occurs on the pairs of electrodes (120, 121) and (170, 171) near the inlet and outlet of the fluidic channel 110. The purpose of electrodes (120, 121) and (170, 171) is to use negative-DEP effect to guide the bioparticles to the center of the fluidic channel 110. In some embodiments, the microfluidic device is configured with only a single pair of electrodes (e.g., one of (120, 121) and (170, 171)). AC voltages at different frequencies are applied to each pair of additional electrodes (130, 131), (140, 141), (150, 151), and (160, 161). Additional electrode pairs can be added in the device 10 to improve the separation capability when necessary.

The geometry of additional pairs of electrodes (130, 131), (140, 141), (150, 151), and (160, 161) is designed in such a manner that the maximum gradient of the electric field occurs at the edges of the (130, 131, 140, 141, 150, 151, 160, 161) electrodes and the lowest gradient of the electric field occurs above the substrate. In consequence, the bioparticles showing a positive DEP effect are attracted to the electrodes and those experiencing negligible DEP effect or negative DEP effect travel in the channel above the electrodes. For instance, the frequency of the AC voltage applied to each pair of electrodes can be set increasingly at 200 kHz, 400 kHz, 800 kHz, and 1600 kHz, respectively. For a particle subject to the DEP effect, there is a transition frequency from negative DEP to positive DEP. In the above arrangement, the particles having a lower transition frequency are attracted to the electrodes closer to the inlet, and the particles having a higher transition frequency are attracted to the electrodes that are closer to the outlet. Those particles having negligible DEP effect or very high transition frequencies leave the channel without being trapped. After wash, one can turn off the AC signals following the sequence that the last pair of electrodes is turned off first and the first pair of electrodes the last. In such case, each time one specific subpopulation of bioparticles can be collected.

The device 10 in FIG. 1(a) can also support single cell analysis that becomes increasingly important to cancer biology, stem cell biology, neurobiology, synthetic biology and biofuel and drug development. During the cell release process from each pair of electrodes, the voltage or frequency of the specific electrode can be suddenly switched off before being restored again. One or few cells that are trapped may be released within such a short time period. Either a microscope can be used to verify if a single cell is released or the downstream electrodes (170, 171) can be used as a cell counter to monitor the number of cells passing. For example, it has been shown that when a cell (particularly a mammalian cell) travels through the space between two electrodes, the impedance (magnitude and phase) between the electrodes changes and this impedance change can be used to count cells.

Figure 1B:
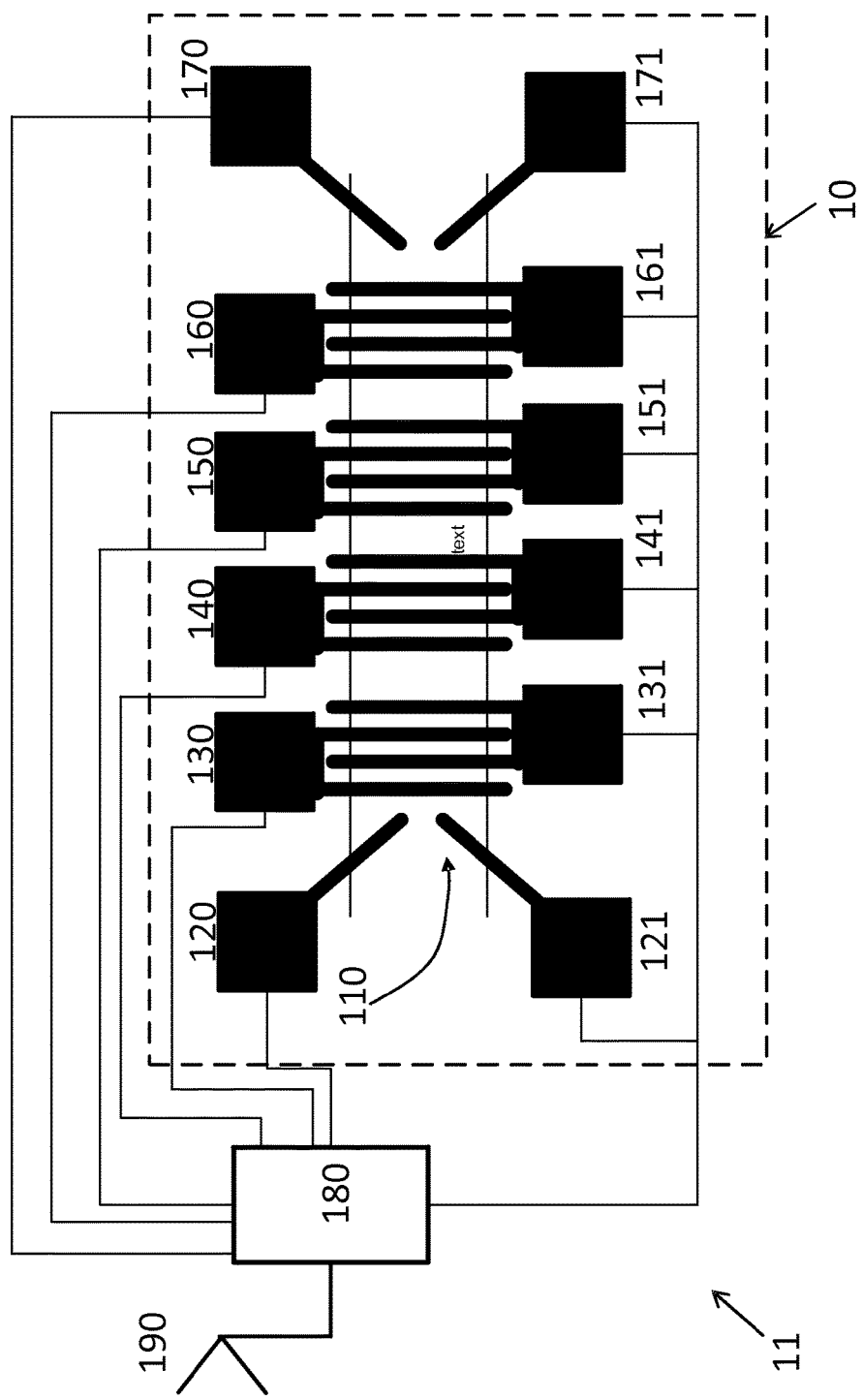
FIG. 1(b) illustrates the microfluidic device of FIG. 1(b) with incorporated electronic circuitry in accordance with an example embodiment.

The device 11 in FIG. 1(b) contains the device 10 in FIG. 1(a) and an integrated circuit to form a microfluidic-electronic lab-on-a-chip device. It should be noted that throughout this document, the term microfluidic-electronic lab-on-a-chip device is sometimes abbreviated as a microfluidic device. In various implementations, such a microfluidic device can be configured to include a fluidic portion and an electronic portion that includes an appropriate antenna/loop for wirelessly receiving RF power from an off-chip RF transmitter to power the chip and its operations. As a specific example, the circuit in FIG. 1(b) includes an inductor antenna 190 that receives wireless RF energy and an integrated circuit 180 that uses the received RF energy to produce AC voltages of (nearly) specific frequencies to electrodes (120, 121), (170, 171), (130, 131), (140, 141), (150, 151), and (160, 161). The integrated circuit 180 may also include memories, registers, switches, processors, busses, and the like, and, such circuit elements may be implemented in ways that are similar to some other integrated circuits. These elements can switch on and off the output voltages to each electrode and store the data such as impedance, phase, or current and transmit the information back to the external world. The antenna 190 typically has a structure of metal loops to inductively couple the power from the transmitter to the on-chip circuit. The amount of power the antenna 190 can couple depends on the geometry and the Ohmic loss of the antenna and the distance from the transmitter. In some implementations, the same antenna 190 may also be used to couple the power from the integrated circuit on the chip back to the transmitter.

Figure 9:
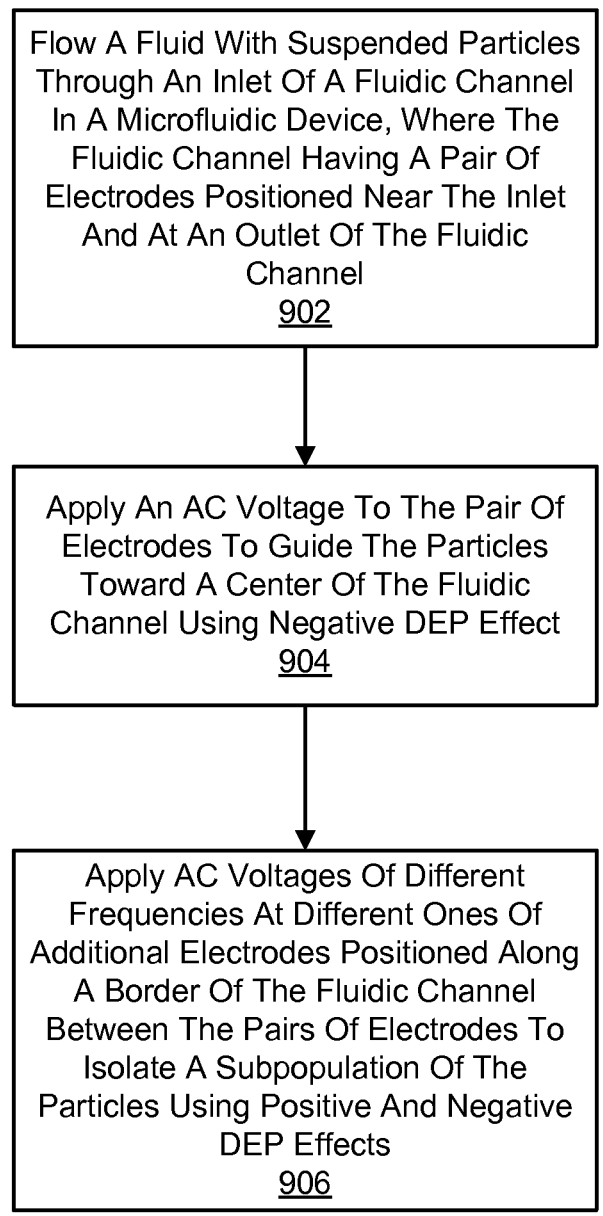
FIG. 9 illustrates a set of operations that can be carried out for isolating a subpopulation of particles suspended in a fluid in accordance with an example embodiment.

FIG. 9 illustrates a set of operations that can be carried out for isolating a subpopulation of particles suspended in a fluid in accordance with an example embodiment. The operation at 902 includes flowing a fluid with suspended particles through an inlet of a fluidic channel in a microfluidic device. The fluidic channel has a pair of electrodes positioned near the inlet and at an outlet of the fluidic channel. Operation 904 includes applying an AC voltage to the pair of electrodes to guide the particles toward a center of the fluidic channel using negative DEP effect. At 906, AC voltages of different frequencies are applied at different ones of additional electrodes positioned along a border of the fluidic channel between the pairs of electrodes to isolate a subpopulation of the particles using positive and negative DEP effects.

Figure 2A:
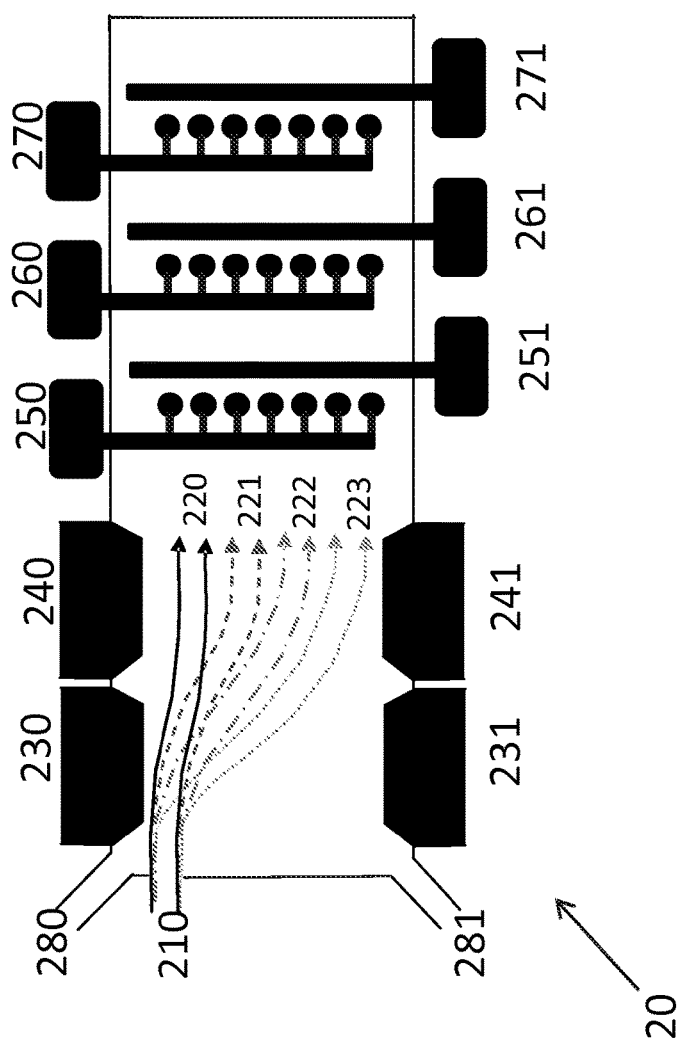
FIG. 2(a) illustrates a microfluidic device in accordance with another example embodiment

FIG. 2(a) illustrates a microfluidic device 20 in accordance with another example embodiment. The device 20 of FIG. 2(a) is capable of allowing sorting and trapping of bioparticles responsive to electric signals of different frequencies. A fluidic sample is introduced from an inlet 210 and sheath flow is introduced from inlet 280 and 281. In some embodiments, additional or fewer sheath inlets may be utilized. The microfluidic channel has a free-flow design to allow the fluid sample spread out transverse to the flow direction. Two pairs of electrodes (230, 231) and (240, 241) near the input of the fluid sample are DC biased to separate particles and molecules electrophoretically. Two pairs, instead of a single pair, of electrodes are used to provide more flexibility and better resolution for particle separation. The particles and molecules are separated into groups, illustrated as 220, 221, 222, 223, according to their charge, isoelectric point, or size due to the electrophoretic (EP) effect. In general, DNA molecules may be near position 223, and the mammalian cells are near the top at position 220 because of their much larger size and mass. Theses coarsely separately bioparticles travel through a series of electrodes (250, 251), (260, 261), (270, 271) with voltages at different frequencies. Each pair of electrodes has an asymmetric geometry as illustrated in FIG. 2(a). Particles experiencing positive DEP effect are attracted to the edge of the circular electrodes, and particles experiencing negative DEP effect take the paths between the circular electrodes where the gradient of the electric field is zero.

One application of the design in FIG. 2(a) is to remove free contaminating DNAs. Each single mammalian cell contains only nanograms of DNA where the flow may contain micrograms of free DNAs within a volume of microliters. Thus for single cell genotyping, the contaminating DNAs may be a thousand times more than the DNA extracted from a single cell. A design such as FIG. 2(a) removes free DNAs by the electrophoretic effect with two pairs of electrodes (230, 231) and (240, 241). When the channel is filled with gels or polymers, the device in FIG. 2(a) can be used to separate DNA segments of different lengths and shapes. The DNA segments with a smaller number of base pairs tend to move towards 223 because of their relatively smaller drag force. These DNA segments can be immobilized to the subsequent electrodes. Another application of the device is to separate and purify proteins. The travel path for proteins near the isoelectric state is least affected by the electrodes (230, 231) and (240, 241). For protein purification and separation, the position of inlet 210 may be moved to the center of the device so that proteins may be separated in either direction depending on the PH value of the electrolyte.

Figure 2B:
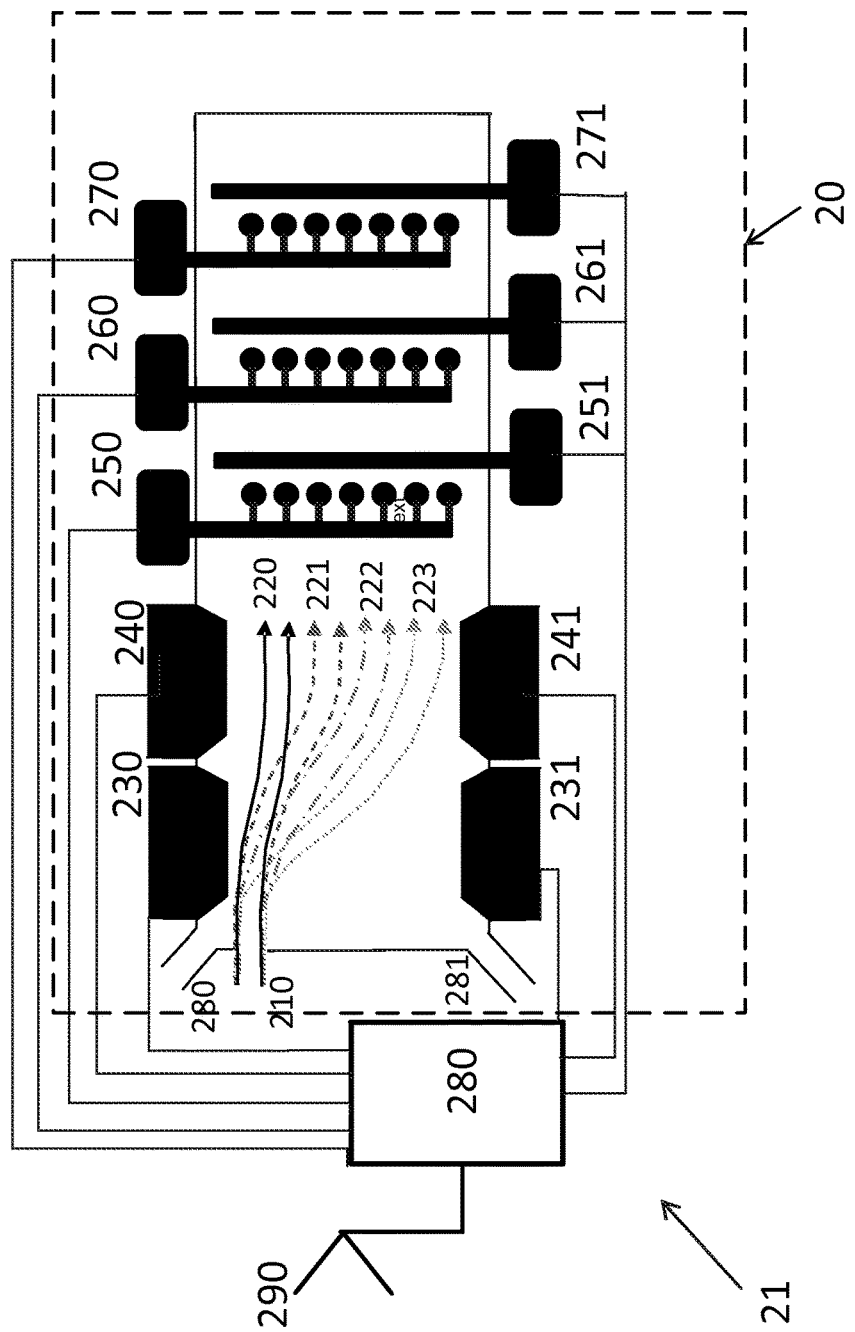
FIG. 2(b) illustrates the microfluidic device of FIG. 2(a) with incorporated electronic circuitry in accordance with an example embodiment

The device 21 in FIG. 2(b) contains the device 20 in FIG. 2(a) and an integrated circuit to form a complete microfluidic-electronic integrated device. The circuit in FIG. 2(b) consists of an antenna 290 and an integrated circuit 280 that produces DC voltage(s) to electrodes (230, 231) (240, 241) and AC voltages of specific frequencies to electrodes (250, 251), (260, 261) and (270, 271). In some implementations, the integrated circuit 280 and the antenna 290 can be configured to have structures similar to 180 and 190 in FIG. 1(b), respectively.

Figure 10:
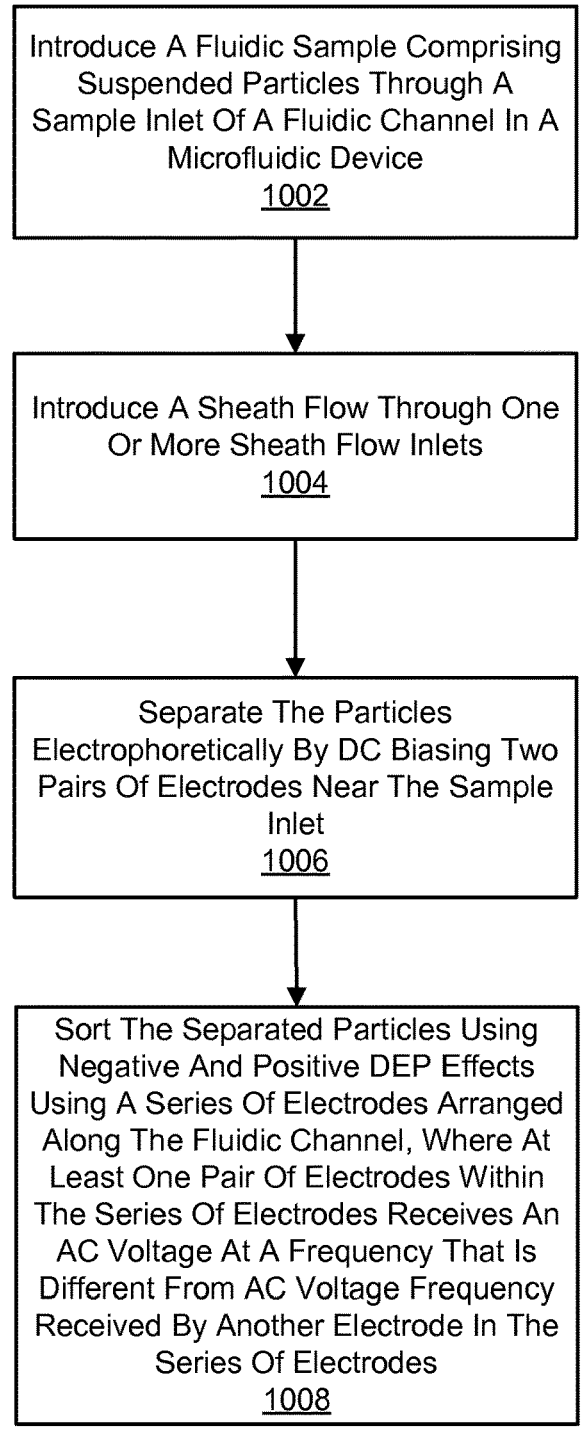
FIG. 10 illustrates a set of operations that can be carried out to sort particles in a microfluidic device in accordance with an example embodiment.

FIG. 10 illustrates a set of operations that can be carried out to sort particles in a microfluidic device in accordance with an example embodiment. At 1002, a fluidic sample comprising suspended particles is introduced through a sample inlet of a fluidic channel in a microfluidic device. At 1004, a sheath flow through one or more sheath flow inlets is introduced in the fluidic channel. At 1006, the particles are electrophoretically separated by DC biasing two pairs of electrodes near the sample inlet. Then, at 1008, the separated particles are sorted using negative and positive DEP effects using a series of electrodes arranged along the fluidic channel, where at least one pair of electrodes within the series of electrodes receives an ac voltage at a frequency that is different from ac voltage frequency received by another electrode in the series of electrodes.

Figure 3A:
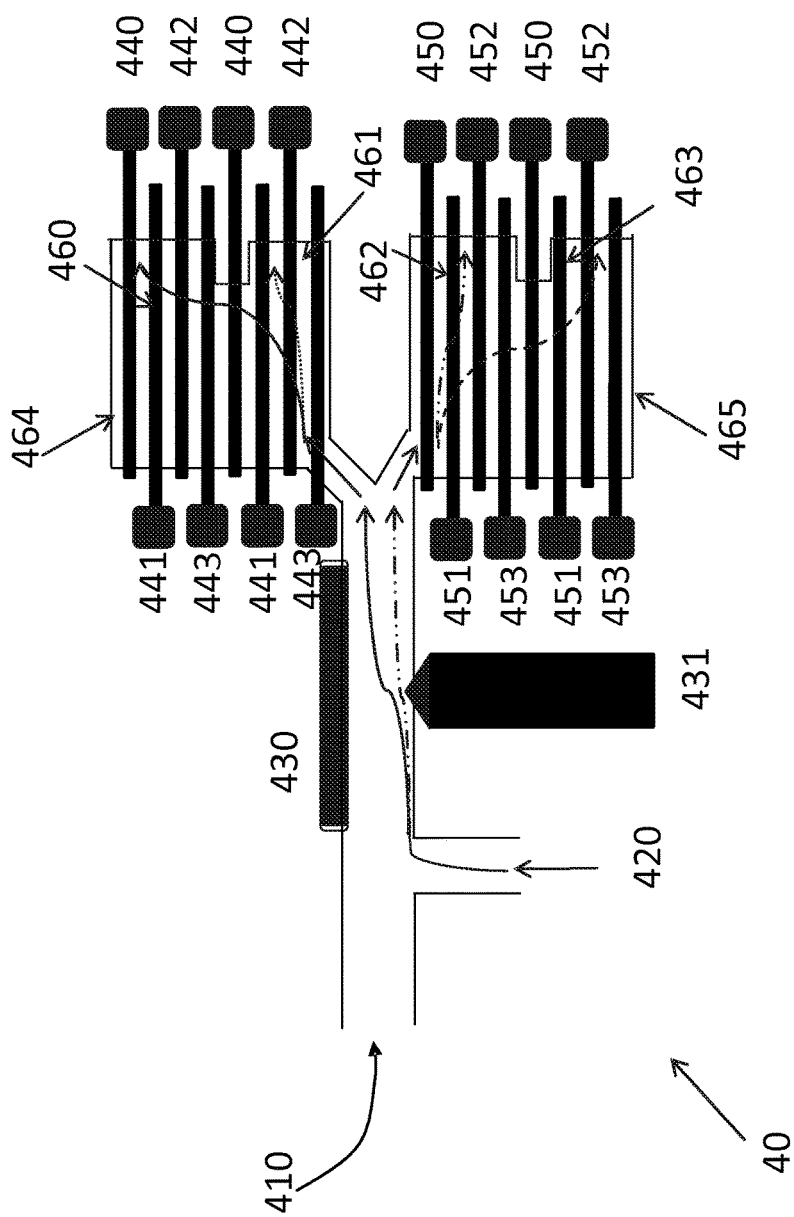
FIG. 3(a) illustrates a microfluidic device in accordance with another example embodiment.

FIG. 3(a) illustrates a microfluidic device 40 in accordance with another example embodiment. The microfluidic device 40 of FIG. 3(a) can be used to effect cell-counting, detection, and sorting of particles. The sample solution is injected from inlet 420 and sheath flow is introduced from inlet 410 so that bioparticles are confined in the lower part of the channel before sorting junction. The microfluidic device has at least two chambers: an upper chamber 464 and a lower chamber 465, where each chamber includes two or more sections 460, 461, 462 and 463. A non-uniform field is generated by the electrode 430 and 431. Cells with different size and Clausius-Mossotti factor experience different amounts of dielectrophoretic force when passing through the electrode pair 430 and 431. Cells experiencing negative DEP will be deflected into upper chambers 464 while cells subject to positive DEP will flow into lower chambers 465. The cells are then subdivided by the travelling DEP force generated by the parallel array electrodes (440, 441, 442, 443) and (450, 451, 452, 453). The phase difference between these electrodes is 90°. For example, if the electrode 440 has a phase of 0°, the electrodes 441, 442, 443 have phases of 90°, 180° and 270°, respectively. Cells subjected to positive traveling DEP are deflected to the sections 460, 463, and those subject to negative DEP are deflected to sections 461, 462. In such a way, cells are grouped to different regions of the device.

Figure 3B:
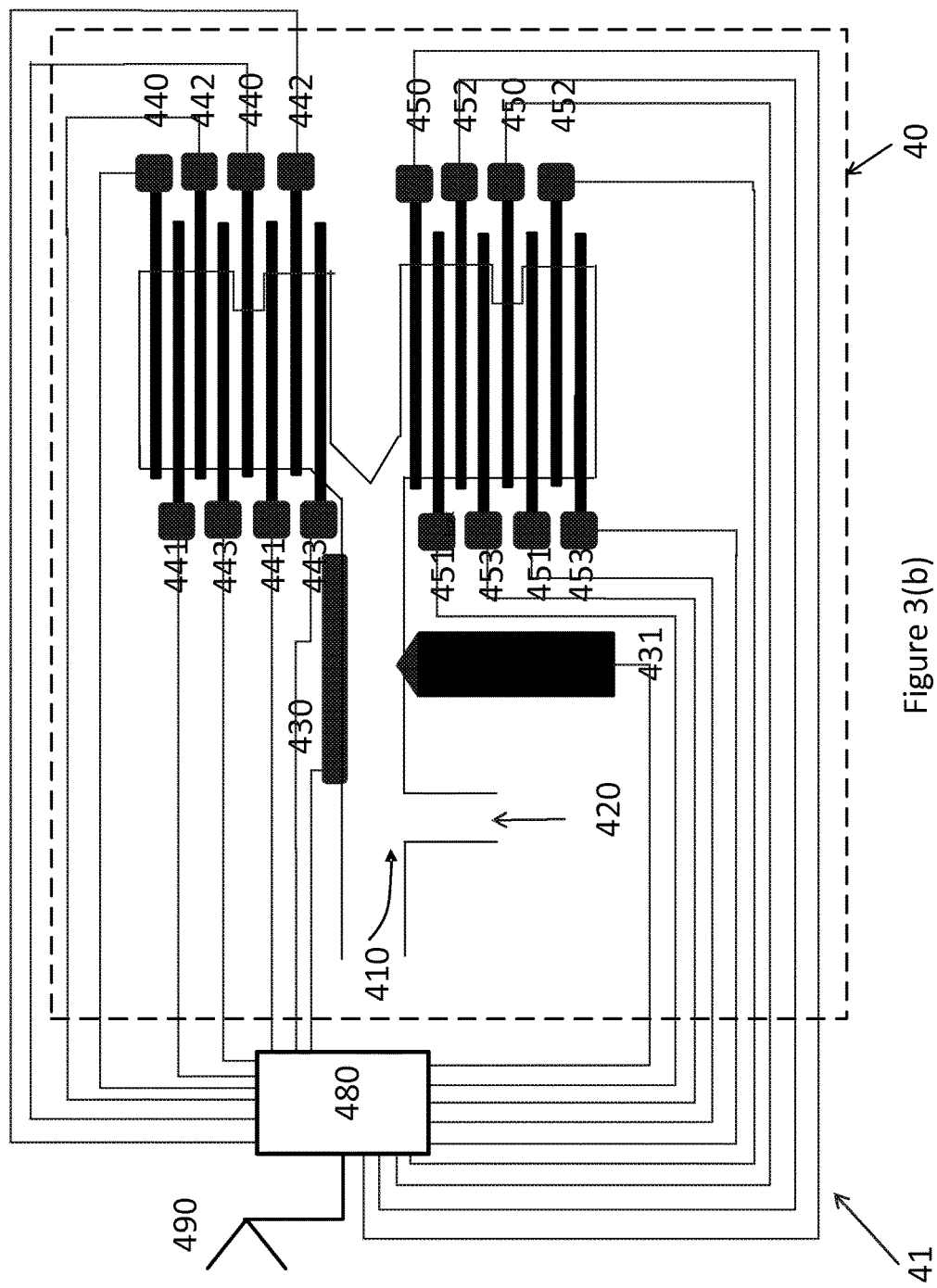
FIG. 3(b) illustrates the microfluidic device of FIG. 3(a) with incorporated electronic circuitry in accordance with an example embodiment

The device 41 in FIG. 3(b) contains the device 40 in FIG. 3(a) and an integrated circuit to form a complete microfluidic-electronic integrated device. The circuit in FIG. 3(b) consists of an antenna 490 and an integrated circuit 480 that produces AC voltages of specific frequencies and phases to electrodes (430, 431), (440, 441,442,443) and (450, 451, 452, 453). The integrated circuit 480 and the antenna 490 are both similar to 180 and 190 in FIG. 1(b).

Figure 11:
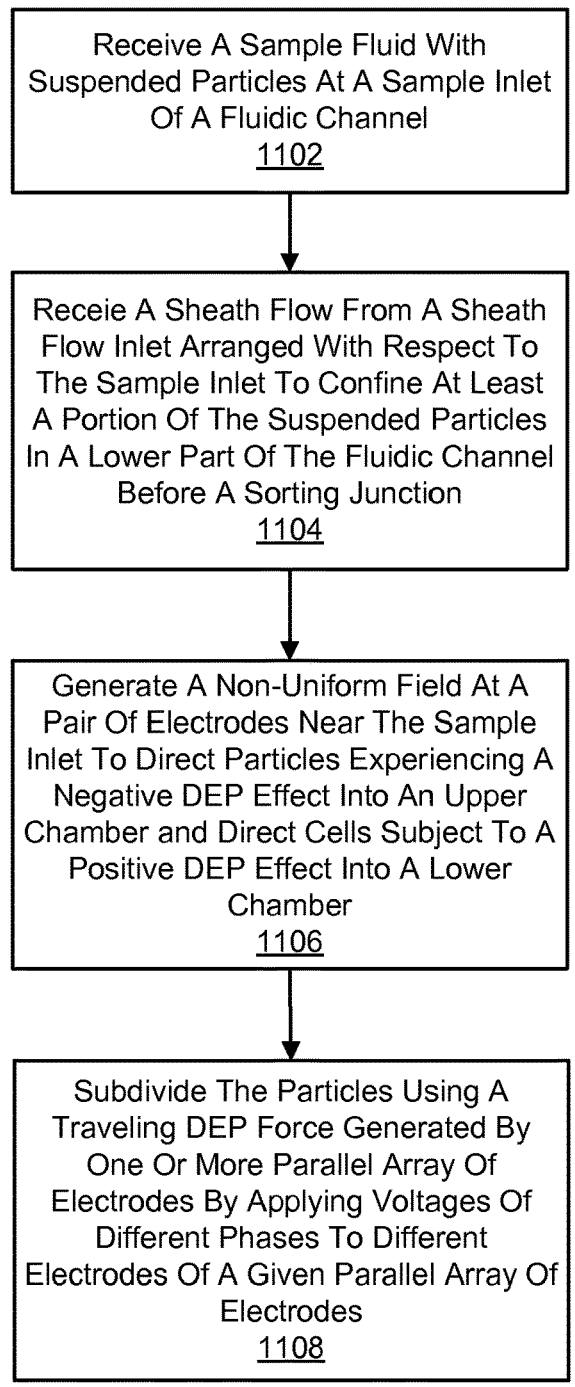
FIG. 11 illustrates a set of operations that can be carried out to sort particles in a microfluidic device in accordance with an example embodiment.

FIG. 11 illustrates a set of operations that can be carried out to sort particles in a microfluidic device in accordance with an example embodiment. At 1102, a sample fluid with suspended particles is received at a sample inlet of a fluidic channel. The operations at 1104 includes receiving a sheath flow from a sheath flow inlet arranged with respect to the sample inlet to confine at least a portion of the suspended particles in a lower part of the fluidic channel before a sorting junction. At 1106, a non-uniform field is generated at a pair of electrodes near the sample inlet to direct particles experiencing a negative DEP effect into an upper chamber while directing cells subject to a positive DEP effect into a lower chamber. At 1108, the particles are subdivided using a traveling DEP force generated by one or more parallel array of electrodes by applying voltages of different phases to different electrodes of a given parallel array of electrodes.

Figure 4A:
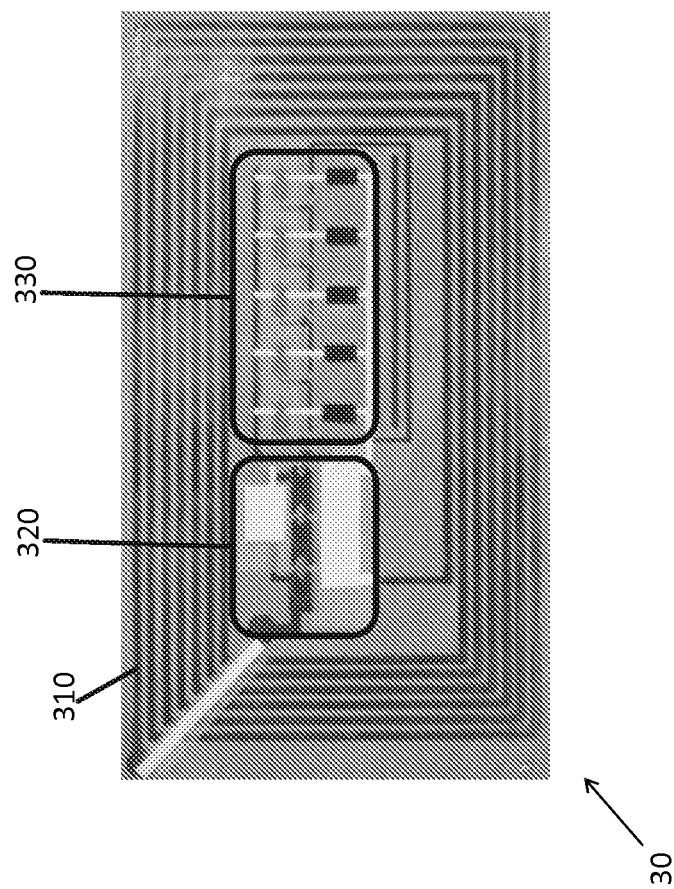
FIG. 4(a) is a photograph of a printed circuit that can be used in the microfluidic devices of the present application.

FIG. 4(a) is a photograph of a printed circuit 30 that can be used in the microfluidic devices of the present application. The picture in FIG. 4(a) shows a printed circuit 30 that is printed on plastic material and consisting of an antenna 310, a rectifier 320, and a 5-stage ring oscillator 330 that generates an AC signal. The rectifier 320 includes components such as diodes and capacitors that convert an AC voltage into a DC voltage. The magnitude of the DC voltage is determined by the number of diodes in series, breakdown voltage of the diodes, the diodes' reverse leakage current, and the value of capacitors. The ring oscillator 330 consists of 5 inverters in series. Each inverter includes a MOS transistor in series with a load resistor or transistor. The oscillation frequency is determined by the sum of the propagation delay of all 5 inverters. For roll-to-roll printed circuits, the material has relatively low mobility which limits the maximum oscillator frequency. The oscillation frequency is also limited by the power consumption which is linearly proportional to the frequency. In many cases, the power consumption, and subsequently the oscillation frequency of the circuit, is also limited by the external load. However, for microfluidic lab-on-a-chip devices, the oscillator drives ions, molecules, and cells which produce very low currents (nanoampers) due to their extremely low mobility. The low power consumption for microfluidic device makes it suitable for wireless powering.

Figure 4B:
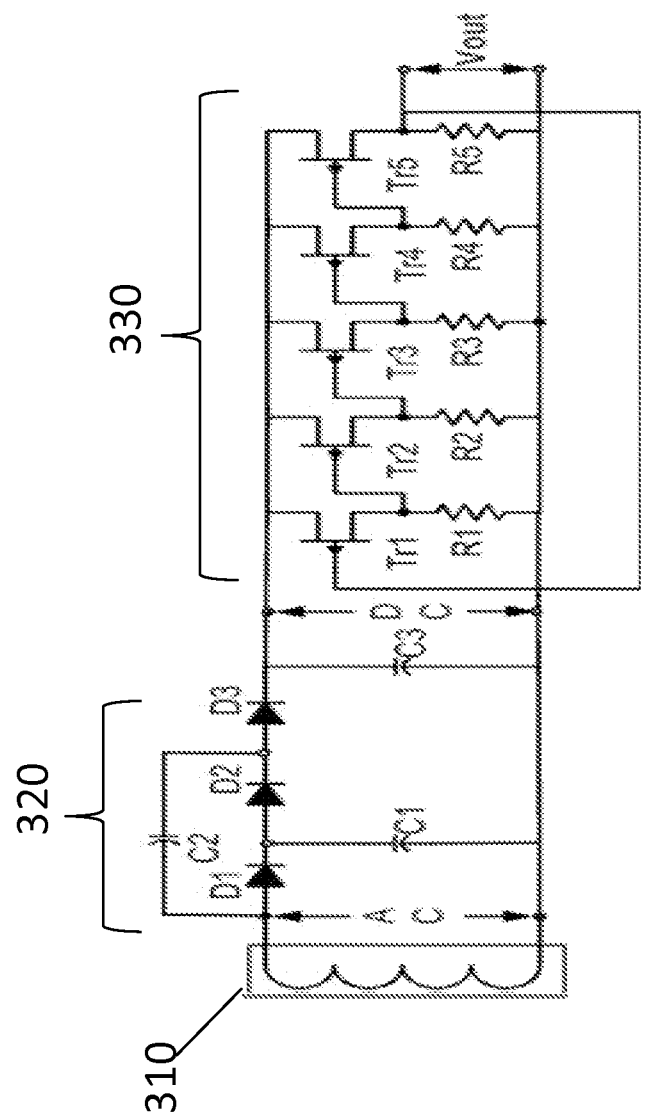
FIG. 4(b) is a schematic diagram of the printed circuit of FIG. 4(a).

FIG. 4(b) shows a schematic diagram of the printed circuit 30 of FIG. 4(a). Power can be transmitted wirelessly from a transmitter (e.g., an RFID reader) to the integrated circuitry of the printed circuit 30 via inductive coupling. When the antenna/inductor 310 of the printed circuit 30 is placed within the electromagnetic field that is transmitted by the transmitter, an AC current is induced between the two terminals of the inductor 310. The two terminals of 310 are connected to the input port of the rectifier 320, which is connected to the ring oscillator 330. Such inductive power coupling mechanism has been applied to RFID (radio frequency identification) and other wireless power transmission devices. This method is particularly attractive to microfluidic lab-on-a-chip device because wireless coupling greatly simplifies the interface between fluid and electronics.

Figure 5A:
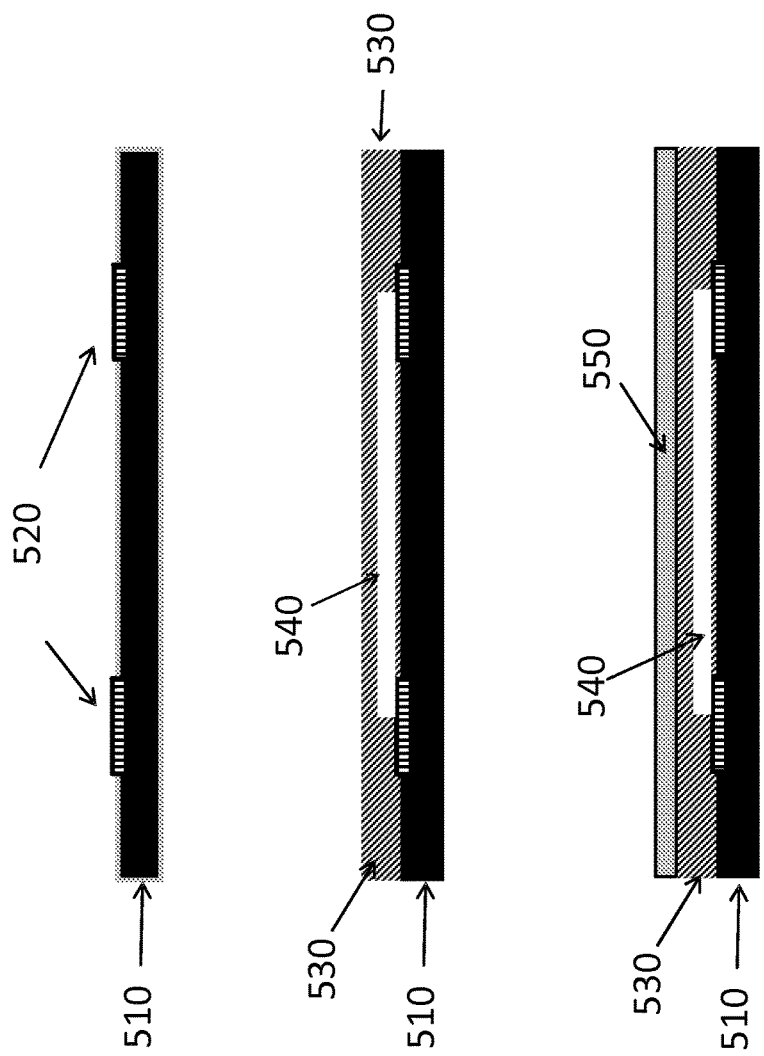
FIG. 5(a) illustrates integrating a printed circuit with a microfluidic device in accordance with an example embodiment.

There are several methods to print integrated circuits such as Roll-to-Roll gravure, inkjet, pad printings, etc. FIG. 5(a) illustrates integrating a printed circuit with a microfluidic device in accordance with an example embodiment. The first step that is shown at the top of FIG. 5(a) is to print electrical circuitry 520 onto a plastic foil substrate or a glass slide 510 using one of the methods mentioned above. The next step, which is shown in the middle row of FIG. 5(a), is to pattern the circuit-printed substrate 510, 520 into hydrophobic and hydrophilic surfaces by employing monolayer chemical (e.g. Poly-allylamine hydrochloride (PAH) and Polyacrylic acid (PAA)) coating. The microfluidic circuit is made such that the spaces 540 used to guide the cells and microbes suspended in the fluid are hydrophilic, while the rest of the parts 530 are hydrophobic. Finally, as shown at the bottom row of FIG. 5(a), a cover slip 550 is placed on top of the device. The patterning is by monolayer processing so that the microfluidic circuitry is invisible to UV/visible light, and it will not disturb optical detection. The sample fluid can be introduced into the patterned area 540 of the slide by capillary force. In such a way, external pumps are eliminated.

Figure 5B:
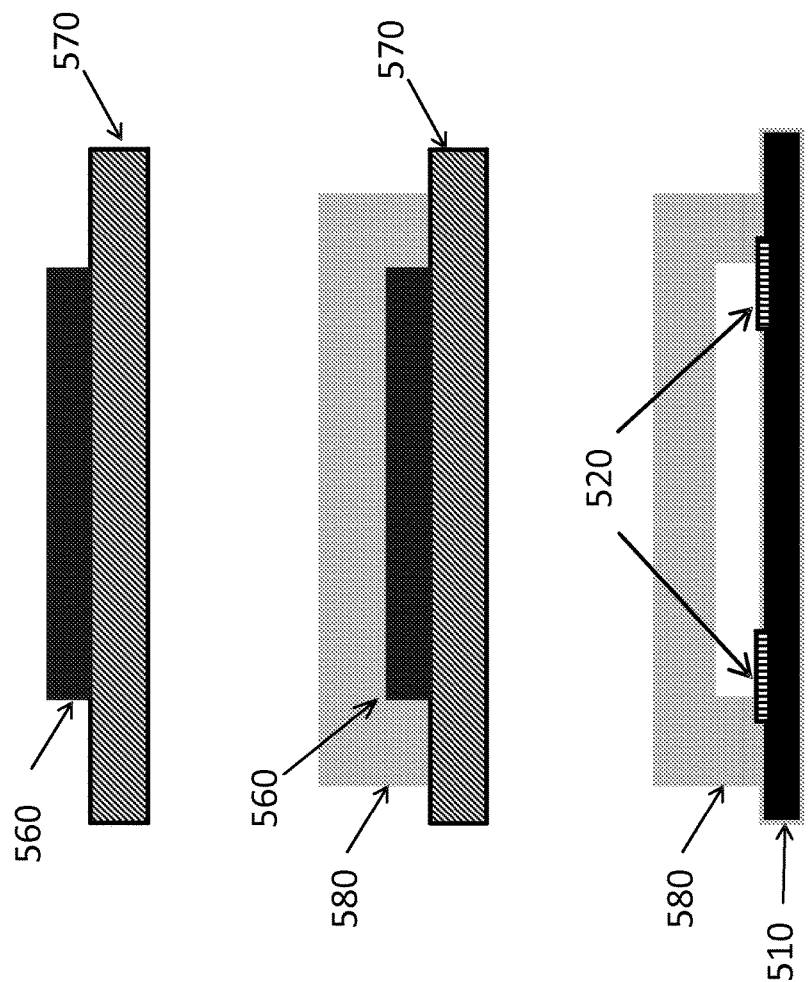
FIG. 5(b) illustrates integrating a printed circuit with a microfluidic device in accordance with another example embodiment.

Another example process for integrating the printed circuit with a microfluidic device is shown in FIG. 5(b). The first step, as illustrated in the top row of FIG. 5(b), is to pattern a mask 560 (e.g., SU8) on a silicon wafer 570 with microfluidic circuit using a photolithography process. In the middle row of FIG. 5(b), the microfluidic circuit is further casted to a polymer sheet 580 (e.g., a Polydimethylsiloxane (PDMS) sheet). Finally, to form fluidic chambers and channels, the cast polymer sheet 580 is separated from the mask 560 and the silicon wafer 570 and is bonded to a substrate 510 that contains the printed circuit 520, as illustrated at the bottom row of FIG. 5(b).

Figure 5C:
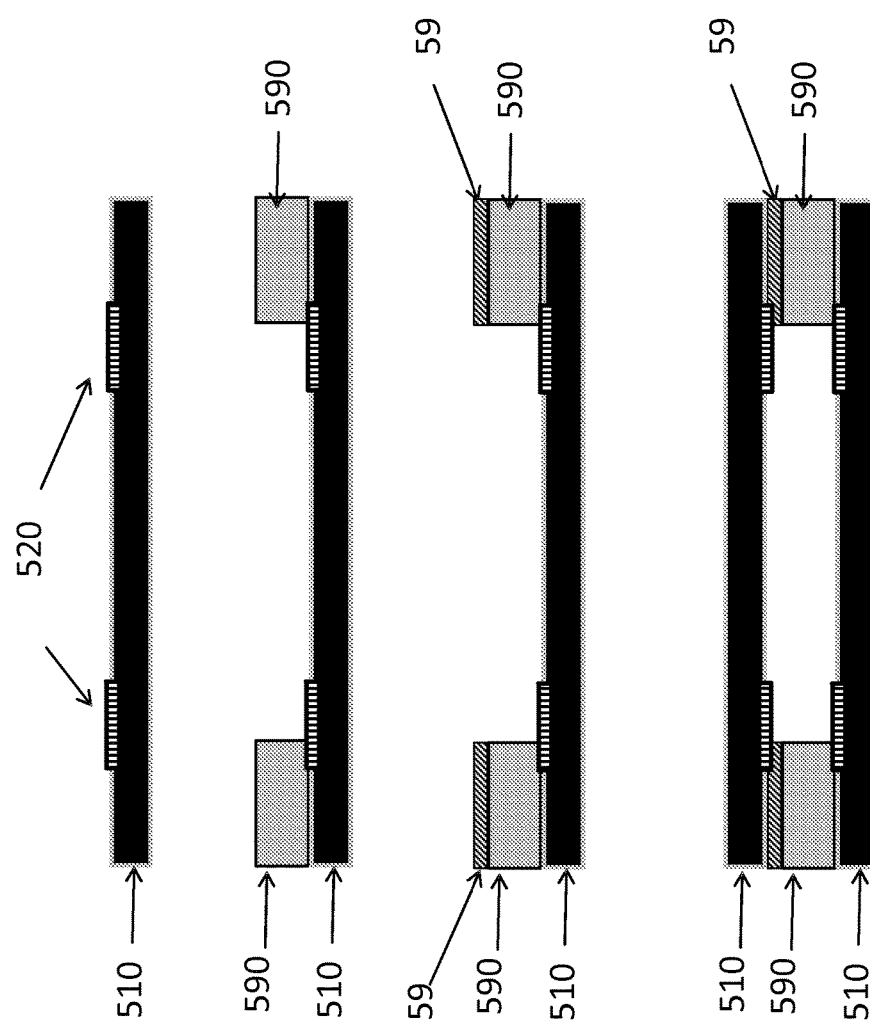
FIG. 5(c) illustrates integrating a printed circuit with a microfluidic device in accordance with another example embodiment.

FIG. 5(c) illustrates integrating a printed circuit with a microfluidic device in accordance with another example embodiment. If 3D flow focusing is needed to further improve bioparticle confinement in the flow, electrodes need to be formed on both the top and the bottom of the channels. In the top two rows of the example process shown in FIG. 5(c), a polymer (e.g., SU8) microfluidic circuit 590 is fabricated on the IC-printed substrate 510 (which includes the printed circuits 520) using photolithography. Then, as illustrated in the third row from top in FIG. 5(c), an adhesion layer 59 is spun on top of the polymer microfluidic circuit 590. Finally, as shown at the bottom row of FIG. 5(c), the IC-printed substrate 510 (which includes the printed circuits 520) is aligned and bonded to another device that is similarly made to form the final device.

An exemplary roll-to-roll printing process for printing the electronic circuitry is described below. A gravure printer with two types of ink units can be used to print the antennas, electrodes, wires, and dielectric layers in a roll-to-roll inline process. The gravure printings can, for example, be carried out under a roll pressure of $0.8 \times 10^{-3}$ Pa and a web speed of 5 meters per minute. Poly(ethylene terephtalate) (PET) foils of 75 μm thick can be chosen as the substrate because of its low cost, good mechanical strength, excellent fatigue resistance at elevated temperatures and high melting temperature of 270° C. For the first step, coiled antennas, wires and bottom electrodes of the diodes and capacitors are printed using silver gravure ink. The viscosity and surface tension of the silver ink are 200 cP and 36 mN/m, respectively. Next, the printed plastic film is passed through a heating chamber (e.g., 150° C.) for 5 seconds for curing to occur. The electrical resistivity of printed antennas, electrodes, and wires is 20 μΩ·cm. The process parameters, such as curing time and printing speed, can be chosen to provide an optimal resonator quality factor (Q) at the desired RF frequency (e.g., 13.56 MHz) for the printed antenna while maintaining high throughput for low production cost. After curing in the first heating chamber, the printed film is passed through the second printing unit to print the dielectric layers on designated areas of wires and capacitors. The ink used to form dielectrics can be BaTiO3 hybrid poly(methyl methacrylate), having a viscosity of 200 cP, a dielectric constant of 13 and a surface tension of 30 mN/m. The thickness of the roll-to-roll-printed dielectric layer in this example embodiment is about 4.5 μm with a surface roughness of 70 nm to prevent high leakage current and early breakdown.

To form Schottky diodes, a semiconducting layer can be printed on the silver electrode and dried at 150° C. for 10 seconds. An example semiconducting ink can be formulated from cobalt-doped ZnO nanowires and polyaniline (PANI). The length of the Co-doped ZnO nanowires ranges from 2 to 10 μm with a diameter of 30 nm. The top electrode can then be printed using Al paste with a low work function of 4.2 eV in order to make Schottky contact to the printed semiconducting layer. The layer of hybrid ZnO nanowires-PANI forms ohmic contacts to the silver electrodes but Schottky contacts to the printed Al electrodes. Finally, Ag ink can be pad printed on gravure printed dielectric layers to form the top electrode for the capacitors. The capacitance of the printed capacitors is 1.2 nF/cm². Using the roll-to-roll printing technique, the integrated circuit on PET foil costs around 3 cents each and the cost can be further reduced to 1 cent. Therefore, the cost is compatible with that of conventional microscope slides and can afford to be disposable.

Figure 12:
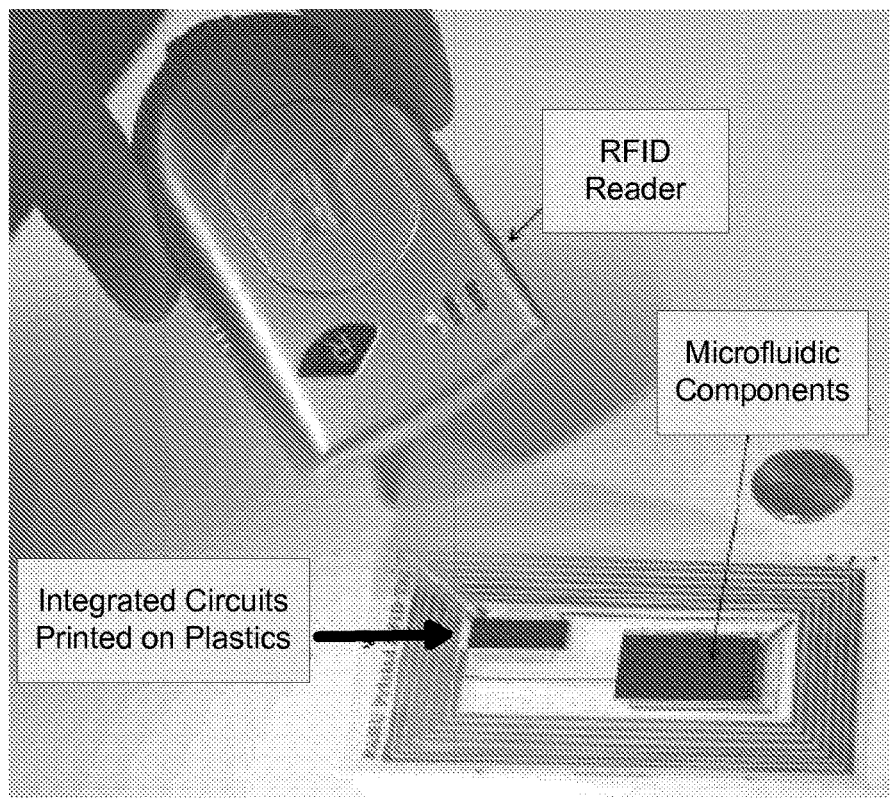
FIG. 12 is a photograph of a microfluidic device that includes microfluidic components and integrated electronics printed on a plastic substrate.

The microfluidic components that are produced according to, for example, one or more of the techniques discussed in connection with FIGS. 5(a) to 5(c), can be mounted on a designated areas of the circuit printed PET substrate using, for example, double adhesive film cut to the size of the glass slide. One or more electrodes can be clamped to the patterned glass to form a microfluidic chamber. Silver paste can be used to connect the outputs of the printed circuit to one or more electrodes of the microchip. An epoxy can be glued on top of the silver paste to strengthen the connection. FIG. 12 is a photograph of the microfluidic device that includes microfluidic components and integrated electronics that are printed on a plastic substrate. An RFID reader can be used to conduct a two-way or one-way remote communication with the microfluidic device.

Figure 6:
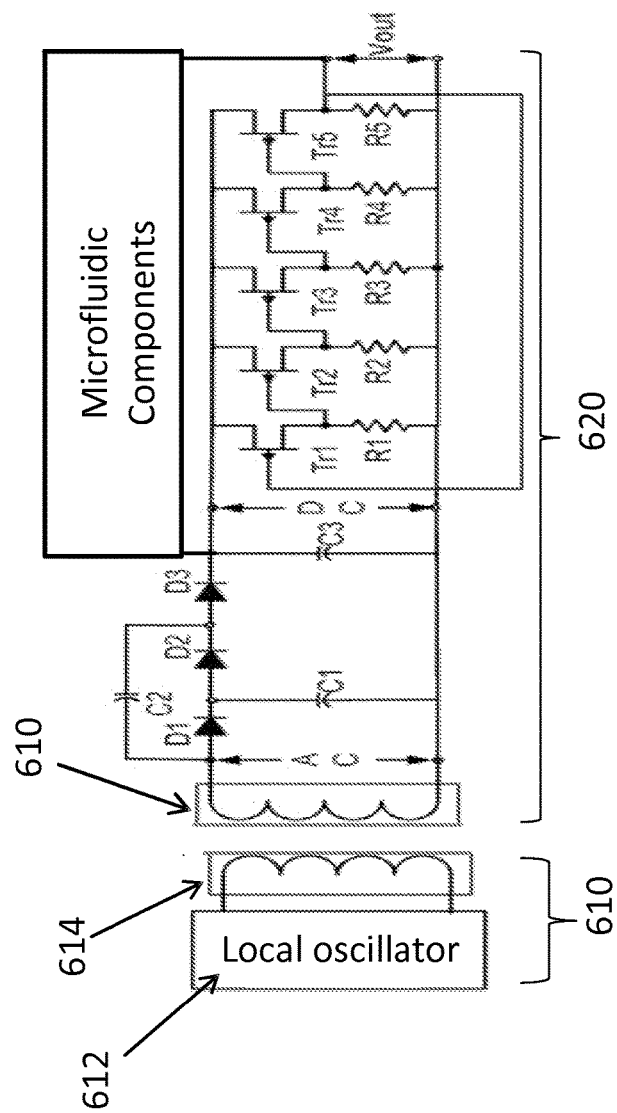
FIG. 6 is a diagram of a microfluidic device that is powered wirelessly by an RF transmitter in accordance with an example embodiment.

FIG. 6 is a schematic of a microfluidic-electronic device 620 (sometime abbreviated as a microfluidic device) that is powered wirelessly by an RF transmitter 610 in accordance with an example embodiment. A transmitter 610 contains a local oscillator 612 and an inductor 614. The local oscillator 612 may operate at different frequencies approved by the FCC. For example, the oscillator may operate at 13.56 MHz. The inductor 614 of the transmitter 610 may have a matched structure to the receiving inductor 610 for maximum power coupling efficiency. The power coupling efficiency also depends on the physical distance between the transmitting inductor 614 and the receiving inductor 610. The efficiency increases as this distance is reduced. Because magnetic field can penetrate most materials, the coupling efficiency is not affected by non-ferromagnetic materials between the two inductors.

As noted earlier in connection with, for example, FIG. 4(a), the induced field in the receiver inductor 610 can be used to generate power for the printed electronic circuitry that are shown in-part in FIG. 6 as part of microfluidic device 620. The electronic circuitry which can include memory elements, diodes, capacitive, inductive and resistive elements, transistors, switches, registers, processors, buses and other electronic circuitry. The circuitry can in turn control the operation of the integrated microfluidic components (which include electrodes, such as the ones that are shown in FIGS. 1(a), 1(b), 2(a), 2(b), 3(a) and 3(b)) to control the flow of fluids within the integrated microfluidic device and to enable trapping, separating, sorting, and detecting particles including bacteria, microbes, virus, DNAs, proteins, parasites, pathogens, yeast, fungi, mammalian cells, beads and nano particles. In one example embodiment, a memory component within the microfluidic device may include processor executable code, which when accessed and executed by the processor within the microfluidic device, configures the microfluidic device to perform various operations, such as sorting, trapping, etc.

Figure 7:
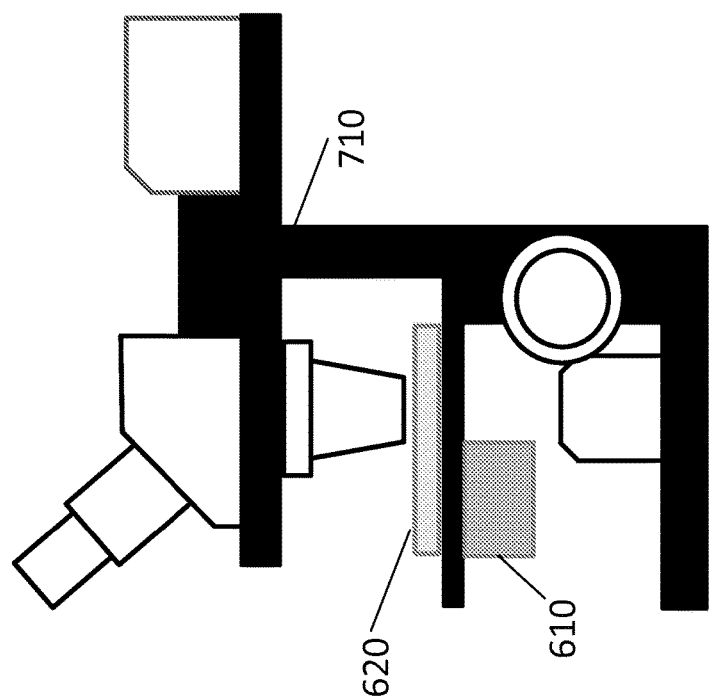
FIG. 7 illustrates a commercial microscope that is configured to operate with a microfluidic device in accordance with an example embodiment.

FIG. 7 illustrates a commercial microscope 710 that is configured to include a wirelessly powered microfluidic-electronic lab-on-a-chip device 620. An RF transmitter 610 is placed under the microscope platform that holds the sample within the 620 microfluidic-electronic lab-on-a-chip device 620. The sample size can be a standard 1"×3" glass slide or other sizes. For inverted microscopes where the objective lens is below the platform, the RF transmitter 610 can be placed on the opposite side of the objective lens.

The disclosed integrated microfluidic-electronic devices can further wirelessly transmit information that is produced by the printed IC of microfluidic-electronic devices. Such information can include handshaking and protocol information that is communicated between the microfluidic-electronic devices and the reader, as well as information obtained from the integrated microfluidic devices such as particle counts and other information. In such a design, the printed circuit of the microfluidic-electronic device functions as a transponder and the RF reader/transmitter also becomes a transceiver.

Figure 8:
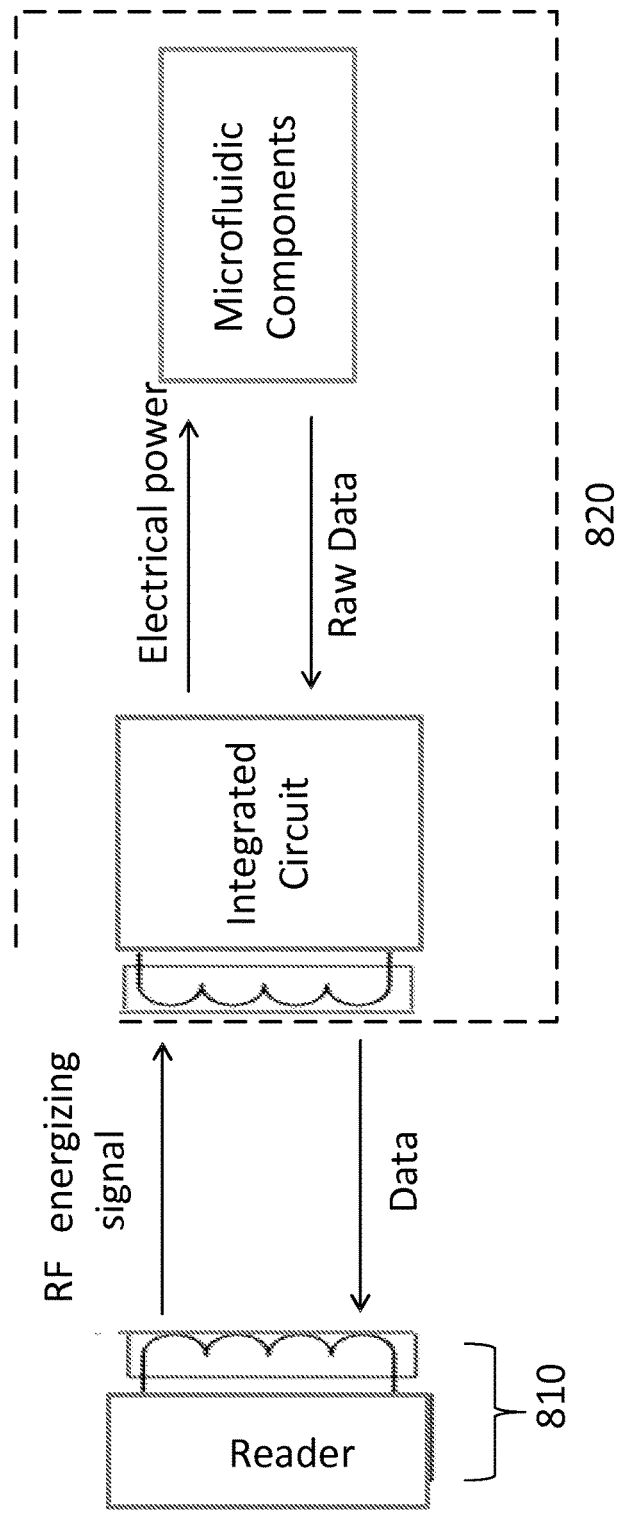
FIG. 8 illustrates a process for communicating information between a microfluidic device and an RF transponder in accordance with an example embodiment.

Various handshaking protocols between an RFID tag and a reader and various data encoding algorithms can be used in implementing the devices described in this document, including protocols and algorithms being used in some commercial RFID devices today. FIG. 8 illustrates a process for communicating information between a microfluidic-electronic device 820 (sometime abbreviated as a microfluidic device) and an RF transponder 810 in accordance with an example embodiment. The microfluidic-electronic device 820 can, for example, be configured to conduct a cell counting operation. The integrated circuit of the microfluidic-electronic device 820 receives sufficient energy from the reader 810 to supply power to the microfluidic components and to configure the device to sense, count, and purify a specific cell type. For example, the impedance (magnitude and phase) change between two electrodes of the microfluidic components can be used to monitor the population of purified cells. Such changes (shown as raw data in FIG. 8) are processed and stored as data in a memory in the integrated circuit, and ultimately transmitted to the reader 810. In one example embodiment, the collected raw data (e.g., the number of detected cells) can modulate a transistor, which is connected to the antenna circuit of the microfluidic-electronic device 820. The modulated transistor electrically shorts the antenna circuit according to the encoded modulation signal (i.e. data), causing voltage modulation of the antenna circuit. The reader 810 then detects the amplitude variation of the tag and uses a peak-detector to extract the modulation data.

While this document contains many specifics, these should not be construed as limitations on the scope of any invention or of what may be claimed, but rather as descriptions of features that may be specific to particular embodiments of particular inventions. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the embodiments described above should not be understood as requiring such separation in all embodiments. Further, only a few implementations and examples are described and other implementations, enhancements and variations can be made based on what is described and illustrated in this document.

What is claimed is:

1. A microfluidic device, comprising:
a fluidic channel in a substrate with an inlet to receive a fluid with particles suspended in the fluid and one or more sheath flow inlets to receive sheath flow;
at least one pair of DC electrodes positioned near the inlet, the at least one pair of DC electrodes configured to electrophoretically separate suspended particles when supplied with a direct current (DC) voltage;
pairs of AC electrodes arranged along the fluidic channel, the pairs of AC electrodes configured to sort the separated particles using one or more of a positive dielectrophoresis (DEP) effect and a negative dielectrophoresis effect when each of the different pairs of AC electrodes are supplied with alternating current (AC) voltages at different frequencies, wherein each pair of AC electrodes includes a circularly shaped electrode and a straight electrode, and wherein the particles experiencing the positive DEP effect are attracted to an edge of the circularly shaped electrodes, and particles experiencing the negative DEP effect are diverted toward paths between the circularly shaped electrodes;

a printed integrated circuit on the substrate configured to produce the AC voltages at the different frequencies, wherein the printed integrated circuit includes one or more active electronic devices; and an inductor on the substrate configured to couple power from a wireless radio frequency (RF) signal emanating from an external transmitter to the integrated circuit.

2. The microfluidic device of claim 1, wherein the fluidic channel has a free-flow design to allow the fluid to spread out transverse to a flow direction.

3. The microfluidic device of claim 1, wherein the at least one pair of DC electrodes are configured to separate the particles into groups according to one or more of a charge, a shape, or a mass based on an electrophoretic (EP) effect.

4. The microfluidic device of claim 1, wherein each of the pairs of AC electrodes is configured to receive an AC voltage that is different in frequency from at least another of the pairs of AC electrodes.

5. The microfluidic device of claim 1, wherein each of the pairs of AC electrodes has an asymmetric geometry.

6. The microfluidic device of claim 1, wherein a gradient of an electric field is zero.

7. The microfluidic device of claim 1, wherein the substrate includes one or more of a glass, a polymer, or a plastic.

8. The microfluidic device of claim 1, wherein the inductor comprises loops to inductively couple the power from the wireless RF signal to the integrated circuit.

9. The microfluidic device of claim 1, wherein the inductor includes silver, and wherein the inductor is a printed inductor printed on the substrate using silver gravure ink.

10. A method of sorting particles, comprising:
receiving a sample fluid with suspended particles at an inlet of a fluidic channel in a substrate and receiving a sheath flow at one or more sheath flow inlets;
electrophoretically separating the suspended particles by supplying at least one pair of direct current (DC) electrodes positioned near the inlet with a DC voltage;
sorting the separated particles via pairs of alternating current (AC) electrodes arranged along the fluidic channel, the sorting using one or more of a positive dielectrophoresis (DEP) effect and a negative dielectrophoresis effect, wherein each of the pairs of AC electrodes are supplied with AC voltages at different frequencies, wherein each pair of AC electrodes includes a circularly shaped electrode and a straight electrode, and wherein the particles experiencing the positive DEP effect are attracted to an edge of the circularly shaped electrodes, and particles experiencing the negative DEP effect are diverted toward paths between the circularly shaped electrodes;
producing the AC voltages at the different frequencies via a printed integrated circuit on the substrate, wherein the printed integrated circuit includes one or more active electronic devices; and
receiving a coupled power at an inductor on the substrate from a wireless radio frequency (RF) signal emanating from an external transmitter to the integrated circuit.

11. The method of sorting particles of claim 10, wherein the fluidic channel has a free-flow design to allow the fluid sample to spread out transverse to a flow direction.

12. The method of sorting particles of claim 10, wherein the at least one pair of DC electrodes are configured to separate the particles into groups according to one or more of a charge, a shape, or a mass based on an electrophoretic (EP) effect.

13. The method of sorting particles of claim 10, wherein each of the pairs of AC of electrodes is configured to receive an AC voltage that is different in frequency from at least another of the pairs of AC electrodes.

14. The method of sorting particles of claim 10, wherein each of the pairs of AC electrodes has an asymmetric geometry.

15. The method of sorting particles of claim 10, wherein a gradient of an electric field is zero.

16. The method of sorting particles of claim 10, wherein the substrate includes one or more of a glass, a polymer, or a plastic.

17. The method of sorting particles of claim 10, wherein the inductor comprises loops to inductively couple the coupled power from the wireless RF signal to the integrated circuit.

18. The method of sorting particles of claim 10, wherein the inductor includes silver, and wherein the inductor is a printed inductor printed on the substrate using silver gravure ink.

* * * * *